United States Patent
Haarstad et al.

(10) Patent No.: US 7,338,434 B1
(45) Date of Patent: Mar. 4, 2008

(54) METHOD AND SYSTEM FOR ORGAN POSITIONING AND STABILIZATION

(75) Inventors: Philip J. Haarstad, Chanhassen, MN (US); Christopher P. Olig, Eden Prairie, MN (US); Paul T. Rothstein, Maple Grove, MN (US); Michael J. Hobday, Lino Lakes, MN (US); David J. S. Kim, Maple Grove, MN (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 593 days.

(21) Appl. No.: 10/643,299

(22) Filed: Aug. 19, 2003

Related U.S. Application Data

(60) Provisional application No. 60/424,243, filed on Nov. 6, 2002, provisional application No. 60/404,969, filed on Aug. 21, 2002.

(51) Int. Cl.
*A61F 2/00* (2006.01)
(52) U.S. Cl. .................. 600/37; 600/201; 600/235
(58) Field of Classification Search ........ 128/897–899; 600/16, 36–37, 103, 114, 121, 125, 127, 129, 600/153, 160, 201, 204, 205, 210, 213, 215–217, 600/219, 227–229, 231–235; 604/164, 264, 604/272, 280; 606/2, 7, 13–16, 32, 41, 129, 606/139, 167, 185, 191, 232–234
See application file for complete search history.

(56) References Cited

U.S. PATENT DOCUMENTS

| | | | |
|---|---|---|---|
| 452,131 A | 5/1891 | Haughawout | |
| 2,590,527 A | 3/1952 | Fluck | |
| 3,577,982 A | 5/1971 | La Par | 128/2 R |
| 3,720,433 A | 3/1973 | Rosfelder | 294/64 R |
| 3,783,873 A | 1/1974 | Jacobs | 128/303 R |
| 3,786,815 A | 1/1974 | Ericson | 128/321 |
| 3,858,926 A | 1/1975 | Ottenhues | 294/64 R |
| 3,916,909 A | 11/1975 | Kletschka et al. | 128/354 |

(Continued)

FOREIGN PATENT DOCUMENTS

DE        G 9004513.0        4/1990

(Continued)

OTHER PUBLICATIONS

Kolessov, et al., "Mammary artery-coronary artery anastomosis as method of treatment for angina pectoris," J. Thorac. Cardio. Surgery, vol. 54, No. 4 (1967), pp. 535-544.

(Continued)

*Primary Examiner*—John P. Lacyk
(74) *Attorney, Agent, or Firm*—Mike Jaro; Jeffrey J. Hohenshell

(57) ABSTRACT

This invention provides a heart positioning device, method and system for positioning, manipulating, holding, grasping, immobilizing and/or stabilizing a heart. The heart positioning device may include a suction head and a shaft with a means for remotely changing the position of the head from a first position axially aligned with the shaft to a second, unaligned position and a sleeve slideably positioned on the shaft and sized to receive the suction head in a compressed condition.

39 Claims, 10 Drawing Sheets

U.S. PATENT DOCUMENTS

| | | | |
|---|---|---|---|
| 3,951,138 A | 4/1976 | Akopov | 128/17 |
| 3,983,863 A | 10/1976 | Janke et al. | 128/1 R |
| 3,999,795 A | 12/1976 | Barker | 294/64 R |
| 4,047,532 A | 9/1977 | Phillips et al. | 128/303 R |
| 4,049,000 A | 9/1977 | Williams | 128/279 |
| 4,049,002 A | 9/1977 | Kletschka et al. | 128/318 |
| 4,096,864 A | 6/1978 | Kletschka et al. | 128/354 |
| 4,306,561 A | 12/1981 | De Medinaceli | 128/303.13 |
| 4,314,568 A | 2/1982 | Loving | 128/327 |
| 4,350,160 A | 9/1982 | Kolesov | 128/334 R |
| 4,366,819 A | 1/1983 | Kaster | 128/334 C |
| 4,368,736 A | 1/1983 | Kaster | 128/334 C |
| 4,428,368 A | 1/1984 | Torii | 128/20 |
| 4,447,227 A | 5/1984 | Kotsanis | 604/95 |
| 4,463,980 A | 8/1984 | Orii | 294/64 R |
| 4,627,421 A | 12/1986 | Symbas et al. | 128/20 |
| 4,637,377 A | 1/1987 | Loop | 128/1 R |
| 4,646,747 A | 3/1987 | Lundbáck | 128/643 |
| 4,688,570 A | 8/1987 | Kramer et al. | 128/305 |
| 4,711,247 A | 12/1987 | Fishman | 128/743 |
| 4,718,418 A | 1/1988 | L'Esperance, Jr. | 128/303.1 |
| 4,726,356 A | 2/1988 | Santilli et al. | 128/20 |
| 4,736,749 A | 4/1988 | Lundback | 128/643 |
| 4,767,142 A | 8/1988 | Takahashi et al. | 294/64.1 |
| 4,808,163 A | 2/1989 | Laub | 604/105 |
| 4,852,552 A | 8/1989 | Chaux | 128/20 |
| 4,854,318 A | 8/1989 | Solem et al. | 128/346 |
| 4,865,019 A | 9/1989 | Phillips | 128/20 |
| 4,892,343 A | 1/1990 | Hall | 294/64.1 |
| 4,904,012 A | 2/1990 | Nishiguchi et al. | 294/64 |
| 4,925,443 A | 5/1990 | Heilman et al. | 600/16 |
| 4,955,896 A | 9/1990 | Freeman | 606/210 |
| 4,962,758 A | 10/1990 | Lasner et al. | 128/41 |
| 4,973,300 A | 11/1990 | Wright | 600/37 |
| 4,989,587 A | 2/1991 | Farley | 128/20 |
| 4,991,578 A | 2/1991 | Cohen | 128/419 D |
| 5,009,660 A | 4/1991 | Clapham | 606/166 |
| 5,011,469 A | 4/1991 | Buckberg et al. | 604/4 |
| 5,053,041 A | 10/1991 | Ansari et al. | 606/148 |
| 5,098,369 A | 3/1992 | Heilman et al. | 600/16 |
| 5,108,412 A | 4/1992 | Krumeich et al. | 606/166 |
| 5,119,804 A | 6/1992 | Anstadt | 12/64 |
| 5,131,905 A | 7/1992 | Grooters | 600/16 |
| 5,133,737 A | 7/1992 | Grismer | 606/205 |
| 5,167,223 A | 12/1992 | Koros et al. | 128/20 |
| 5,171,254 A | 12/1992 | Sher | 606/166 |
| 5,207,467 A | 5/1993 | Smith | 294/64.1 |
| 5,256,132 A * | 10/1993 | Snyders | 600/16 |
| 5,287,861 A | 2/1994 | Wilk | 128/898 |
| 5,290,082 A | 3/1994 | Palmer et al. | 294/64.1 |
| 5,300,087 A | 4/1994 | Knoepfler | 606/207 |
| 5,324,087 A | 6/1994 | Shimose et al. | 294/64.1 |
| 5,336,252 A * | 8/1994 | Cohen | 607/119 |
| 5,365,921 A | 11/1994 | Bookwalter et al. | 128/20 |
| 5,372,124 A | 12/1994 | Takayama et al. | 128/4 |
| 5,374,277 A | 12/1994 | Hassler | 606/207 |
| 5,383,840 A | 1/1995 | Heilman et al. | 600/17 |
| 5,417,709 A | 5/1995 | Slater | 606/205 |
| 5,425,705 A | 6/1995 | Evard et al. | 604/28 |
| 5,437,651 A | 8/1995 | Todd et al. | 604/313 |
| 5,452,733 A | 9/1995 | Sterman et al. | 128/898 |
| 5,472,438 A | 12/1995 | Schmit et al. | 606/1 |
| 5,503,617 A | 4/1996 | Jako | 600/201 |
| 5,509,890 A | 4/1996 | Kazama | 600/37 |
| 5,545,123 A | 8/1996 | Ortiz et al. | 600/235 |
| 5,553,198 A * | 9/1996 | Wang et al. | 700/245 |
| 5,556,147 A | 9/1996 | Somekh et al. | 294/64.1 |
| 5,607,421 A | 3/1997 | Jeevanandam et al. | 606/15 |
| 5,613,937 A | 3/1997 | Garrison et al. | 600/201 |
| 5,657,429 A * | 8/1997 | Wang et al. | 700/251 |
| 5,667,624 A | 9/1997 | Akimoto et al. | 156/389 |
| 5,702,420 A | 12/1997 | Sterling et al. | 606/205 |
| 5,727,569 A | 3/1998 | Benetti et al. | 128/898 |
| 5,730,757 A | 3/1998 | Benetti et al. | 606/198 |
| 5,749,892 A | 5/1998 | Vierra et al. | 600/204 |
| 5,772,583 A | 6/1998 | Wright et al. | 600/232 |
| 5,782,746 A | 7/1998 | Wright | 600/37 |
| 5,799,661 A * | 9/1998 | Boyd et al. | 128/898 |
| 5,807,243 A | 9/1998 | Vierra et al. | 600/204 |
| 5,827,216 A | 10/1998 | Igo et al. | 604/21 |
| 5,836,311 A | 11/1998 | Borst et al. | 128/897 |
| 5,865,730 A | 2/1999 | Fox et al. | 600/228 |
| 5,875,782 A | 3/1999 | Ferrari et al. | 128/898 |
| 5,876,332 A | 3/1999 | Looney | 600/227 |
| 5,885,271 A | 3/1999 | Hamilton et al. | 303/1 |
| 5,888,247 A | 3/1999 | Benetti | 623/66 |
| 5,891,017 A | 4/1999 | Swindle et al. | 600/205 |
| 5,894,843 A | 4/1999 | Benetti et al. | 128/898 |
| 5,906,607 A | 5/1999 | Taylor et al. | 606/1 |
| 5,927,284 A | 7/1999 | Borst et al. | 128/898 |
| 5,947,896 A | 9/1999 | Sherts et al. | 600/229 |
| 5,957,835 A | 9/1999 | Anderson et al. | 600/201 |
| 5,967,972 A | 10/1999 | Santilli et al. | 600/232 |
| 5,976,080 A | 11/1999 | Farascioni | 600/213 |
| 5,976,171 A | 11/1999 | Taylor | 606/198 |
| 5,984,864 A | 11/1999 | Fox et al. | 600/201 |
| 6,007,486 A | 12/1999 | Hunt et al. | 600/205 |
| 6,015,378 A | 1/2000 | Borst et al. | 600/37 |
| 6,017,304 A | 1/2000 | Vierra et al. | 600/204 |
| 6,019,722 A * | 2/2000 | Spence et al. | 600/210 |
| 6,030,340 A | 2/2000 | Maffei et al. | 600/213 |
| 6,032,672 A | 3/2000 | Taylor | 128/898 |
| 6,033,362 A | 3/2000 | Cohn | 600/213 |
| 6,036,641 A | 3/2000 | Taylor et al. | 600/231 |
| 6,050,266 A | 4/2000 | Benetti et al. | 128/898 |
| 6,063,021 A | 5/2000 | Hossain et al. | 600/37 |
| 6,071,235 A | 6/2000 | Furnish et al. | 600/235 |
| 6,071,295 A | 6/2000 | Takahashi | 606/191 |
| 6,102,854 A | 8/2000 | Cartier et al. | 600/228 |
| 6,110,187 A | 8/2000 | Donlon | 606/151 |
| 6,113,534 A | 9/2000 | Koros et al. | 600/213 |
| 6,139,492 A | 10/2000 | Vierra et al. | 600/204 |
| 6,152,874 A | 11/2000 | Looney et al. | 600/214 |
| 6,159,201 A | 12/2000 | Hamilton et al. | |
| 6,174,307 B1 * | 1/2001 | Daniel et al. | 606/15 |
| 6,210,323 B1 | 4/2001 | Gilhuly et al. | 600/210 |
| 6,213,941 B1 | 4/2001 | Benetti et al. | 600/235 |
| 6,238,334 B1 | 5/2001 | Easterbrook, III et al. | 600/16 |
| 6,251,065 B1 | 6/2001 | Kochamba et al. | 600/37 |
| 6,258,023 B1 | 7/2001 | Rogers et al. | 600/37 |
| 6,328,688 B1 | 12/2001 | Borst | |
| 6,334,843 B1 | 1/2002 | Borst | |
| 6,336,898 B1 | 1/2002 | Borst | |
| 6,350,229 B1 | 2/2002 | Borst | |
| 6,364,826 B1 | 4/2002 | Borst | |
| 6,371,906 B1 | 4/2002 | Borst | |
| 6,371,910 B1 | 4/2002 | Zwart et al. | 600/207 |
| 6,394,948 B1 | 5/2002 | Borst | |
| 6,394,951 B1 | 5/2002 | Taylor et al. | 600/210 |
| 6,395,015 B1 | 5/2002 | Borst | |
| 6,459,926 B1 | 10/2002 | Nowlin et al. | |
| 6,464,629 B1 | 10/2002 | Borst | |
| 6,464,630 B1 | 10/2002 | Borst | |
| 6,468,265 B1 | 10/2002 | Evans | |
| 6,488,618 B1 | 12/2002 | Paolitto et al. | 600/37 |
| 6,503,245 B2 | 1/2003 | Palmer et al. | 606/1 |
| 6,506,149 B2 | 1/2003 | Peng et al. | 600/37 |
| 6,511,416 B1 | 1/2003 | Green, II et al. | 600/37 |
| 6,517,563 B1 * | 2/2003 | Paolitto et al. | 606/205 |
| 6,551,242 B1 | 4/2003 | Furnish et al. | 600/213 |
| 6,558,314 B1 | 5/2003 | Adelman et al. | 600/37 |
| 6,585,643 B2 | 7/2003 | Clem et al. | 600/210 |
| 6,589,166 B2 | 7/2003 | Knight et al. | 600/205 |
| 6,602,183 B1 | 8/2003 | Levi et al. | 600/37 |

| | | | |
|---|---|---|---|
| 6,602,189 B1 | 8/2003 | Bennetti et al. | 600/252 |
| 6,607,479 B1 | 8/2003 | Kochamba et al. | 600/37 |
| 6,740,028 B2 | 5/2004 | Borst | |
| 6,755,780 B2 | 6/2004 | Borst | |
| 6,936,001 B1* | 8/2005 | Snow | 600/37 |
| 7,048,683 B2 | 5/2006 | Borst | |
| 2001/0041827 A1 | 11/2001 | Spence et al. | 600/201 |
| 2002/0045888 A1 | 4/2002 | Ramans | |
| 2002/0082612 A1 | 6/2002 | Moll | |
| 2002/0099268 A1 | 7/2002 | Paul et al. | 600/201 |
| 2002/0128552 A1 | 9/2002 | Nowlin | |
| 2002/0137989 A1 | 9/2002 | Clem et al. | 600/210 |
| 2002/0161277 A1 | 10/2002 | Mansvelt-Beck et al. | |
| 2002/0165434 A1 | 11/2002 | Williamson, IV et al. | 600/201 |
| 2003/0013949 A1 | 1/2003 | Moll | |
| 2003/0055410 A1 | 3/2003 | Evans | |
| 2003/0078470 A1 | 4/2003 | Borst | |
| 2003/0078471 A1* | 4/2003 | Foley et al. | 600/37 |
| 2003/0083554 A1 | 5/2003 | Paolitto et al. | 600/205 |
| 2003/0088150 A1 | 5/2003 | Green, II et al. | 600/37 |
| 2003/0125604 A1 | 7/2003 | Kochamba et al. | 600/37 |
| 2003/0158463 A1 | 8/2003 | Julian et al. | |
| 2003/0216715 A1 | 11/2003 | Moll | |
| 2004/0167549 A1 | 8/2004 | Borst | |
| 2005/0033270 A1 | 2/2005 | Ramans | |
| 2005/0107808 A1 | 5/2005 | Evans | |
| 2006/0036128 A1 | 2/2006 | Borst | |
| 2006/0178559 A1 | 8/2006 | Kumar | |
| 2006/0241414 A1 | 10/2006 | Nowlin | |

FOREIGN PATENT DOCUMENTS

| | | |
|---|---|---|
| DE | 29708050 | 5/1997 |
| EP | 0 167 345 A1 | 1/1986 |
| EP | 0 293 760 A3 | 5/1988 |
| EP | 0 432 560 A2 | 6/1991 |
| EP | 0 432 560 A3 | 6/1991 |
| EP | 0 630 629 A1 | 12/1994 |
| EP | 0 668 058 A1 | 8/1995 |
| EP | 0 808 606 A1 | 11/1997 |
| EP | 0 908 139 A1 | 4/1999 |
| EP | 0 919 193 A1 | 6/1999 |
| EP | 0 920 835 A1 | 6/1999 |
| EP | 0 993 806 A2 | 4/2000 |
| EP | 0 993 806 A3 | 6/2000 |
| GB | 2 140 695 | 12/1984 |
| GB | 2 214 428 A | 9/1989 |
| GB | 2 233 561 A | 1/1991 |
| GB | 2 214 428 B | 6/1991 |
| GB | 2 267 827 A | 12/1993 |
| WO | WO 87/04081 | 7/1987 |
| WO | WO 88/00481 | 1/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/40751 | 11/1997 |
| WO | WO 98/10705 | 3/1998 |
| WO | WO 98/17182 | 4/1998 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/15119 | 3/2000 |
| WO | WO 03/001969 | 1/2003 |
| WO | WO 03/001998 | 1/2003 |

OTHER PUBLICATIONS

Favaloro, et al., "Direct Myocardial Revascularization by Saphenous Vein Graft," The Annals of Thoracic Surgery, vol. 10, No. 2 (1970), pp. 97-111.

Riahi, et al., "A simple technique and device to provide a bloodless operative field in coronary artery surgery without cross-clamping the aorta," J. Thorac. Cardio. Surgery, vol. 66, No. 6 (1973), pp. 974-978.

Trapp, et al., "To Use or Not to Use the Pump Oxygenator in Coronary Bypass Operations," The Annals of Thoracic Surgery, vol. 19, No. 1 (1975), pp. 108-111.

Zumbro, et al., "A Prospective Evaluation of the Pulsatile Assist Device," The Annals of Thoracic Surgery, vol. 28, No. 3 (1979), pp. 269-273.

Akins, et al., "Preservation of interventricular septal function in patients having coronary artery bypass grafts without cardiopulmonary bypass," American Heart Journal, vol. 107, No. 2 (1984), pp. 304-309.

Archer, et al., "Coronary Artery Revascularization Without Cardiopulmonary Bypass," Texas Heart Institute Journal, vol. 11, No. 1 (1984), pp. 52-57.

Buffolo, et al., "Direct Myocardial Revascularization without Cardiopulmonary Bypass," Thorac. Cardiovasc. Surgeon 33 (1985), pp. 26-29.

Benetti, "Direct coronary surgery with saphenous vein bypass without either cardioipulmonary bypass or cardiac arrest," J. Cardiovasc. Surg. vol. 26, No. 3 (1985), pp. 217-222.

Kresh, et al., "Heart-mechanical Assist Device Interaction," Trans. Am. Soc. Artif. Intern. Organs, vol. 32 (1986), pp. 437-443.

Ballantyne, et al., "Delayed Recovery of Severely 'Stunned' Myocardium with the Support of a Left Ventricular Assist Device after Coronary Artery Bypass Graft Surgery," Journal of American College of Cardiology, vol. 10, No. 3 (1987), pp. 710-712.

Ruzevich, et al., "Long-term Follow-up of Survivors of Postcardiotomy Circulatory Support," Trans. Am. Soc. Artif. Intern. Organs, vol. 34 (1988), pp. 116-124.

McGee, et al., "Extended Clinical Support with an Implantable Left Ventricular Assist Device," Trans. Am. So. Artif. Intern. Organs, vol. 35 (1989), pp. 614-616.

Richenbacher, et al., "Current Status of Cardiac Surgery: A 40 Year Review," JACC, vol. 14, No. 3 (1989), pp. 535-544.

Scholz, et al., "Transfemoral Placement of the Left Ventricular Assist Device 'Hemopump' During Mechanical Resuscitation," Thorac. Cardiovasc. Surgn., vol. 38 (1990), pp. 69-72.

Anstadt, et al., "Direct Mechanical Ventricular Actuation for Cardiac Arrest in Humans," Chest, vol. 100, No. 1 (1991), pp. 86-92.

Benetti, et al., "Direct Myocardial Revascularization without Extracorporeal Circulation," Chest, vol. 100, No. 2 (1991) pp. 312-316.

Pfister, et al., "Coronary Artery Bypass Without Cardiopulmonary Bypass," Ann. Thorac. Surg., vol. 54, No. 6 (1992), pp. 1085-1092.

Lönn, et al., "Coronary Artery Operation Supported by the Hemopump: An Experimental Study on Pig," Ann. Thorac. Surg., vol. 58, No. 1 (1994), pp. 516-518.

"Regional Cardiac Wall Immobilization for Open Chest and Closed Chest Coronary Artery Bypass Grafting on the Beating Heart: The 'Octopus' Method," Circulation, vol. 92, No. 8 Supplement 1 (1995), p. I-177.

Robinson, et al., "A Minimally Invasive Surgical Method for Coronary Revascularization—Preliminary Experience in Five Patients," Circulation, vol. 92, No. 8 (1995), I-176.

Borst, et al., "Coronary Artery Bypass Grafting Without Cardiopulmonary Bypass and Without Interruption of Native Coronary Flow Using a Novel Anastomosis Site Restraining Device ('Octopus')," JACC, vol. 27, No. 6 (1996), pp. 1356-1364.

Gacioch, et al., "Cardiogenic Shock Complicating Acute Myocardial Infarction: The Use of Coronary Angioplasty and the Integration of the New Support Devices into Patient Management," JACC, vol. 19, No. 3 (1992), pp. 647-653.

Fanning, et al., "Reoperative Coronary Artery Bypass Grafting Without Cardiopulmonary Bypass," Ann. Thorac. Surg., Vo. 55, No. 2 (1993), pp. 486-489.

Fonger, et al., "Enhanced Preservation of Acutely Ischemic Myocardium With Transseptal Left Ventricular Assist," Ann. Thorac. Surg., vol. 57, No. 3 (1994), pp. 570-575.

Lavergne, et al., "Transcatheter Radiofrequency Ablation of Atrial Tissue Using a Suction Catheter," PACE, vol. 12 (1989), Part II, pp. 177-186.

Stevens, et al., Abstract: "Closed Chest Coronary Artery Bypass with Cardioplegic Arrest in the Dog," 67th Scientific Sessions.

Trapp, et al., "Placement of Coronary Artery Bypass Graft Without Pump Oxygenator," Ann. Thorac. Surg., vol. 19, No. 1 (1975), pp. 1-9.

Gründeman, et al., "Experimental videothoracoscopic cannulation of the left atrial appendix," Surg. Endosc., (1993) 7:511-513.

Calafiore, et al., "The LAST Operation: Techniques and Results Before and After the Stabilization Era," Ann. Thorac. Surg. (1998); 66:998-1001.

Konishi, et al., "Hybrid-Type Stabilizer for Off-Pump Direct Coronary Artery Bypass Grafting," Ann. Thorac. Surg., (1998) 66:961-2.

DelRossi, et al., "A New Retractor to Aid in Coronary Artery Surgery," Ann. Thorac. Surg., vol. 36, No. 1 (1983), pp. 101-102.

Westaby, et al, "Less Invasive Coronary Surgery: Consensus From the Oxford Meeting," Ann. Thorac. Surg. (1996) 62:924-31.

Roux, et al., "New Helper Instrument in Cardiac Surgery," Ann. Thorac. Surg., (1989) 48:595-6.

Kolessov, "The Surgery of Coronary Arteries of the Heart," Leningrad, Meditsina, 1997, p. 360 (Russian article).

Kolessov, "The Surgery of Coronary Arteries of the Heart," Leningrad, Meditsina, 1997, p. 360 (English translation).

* cited by examiner

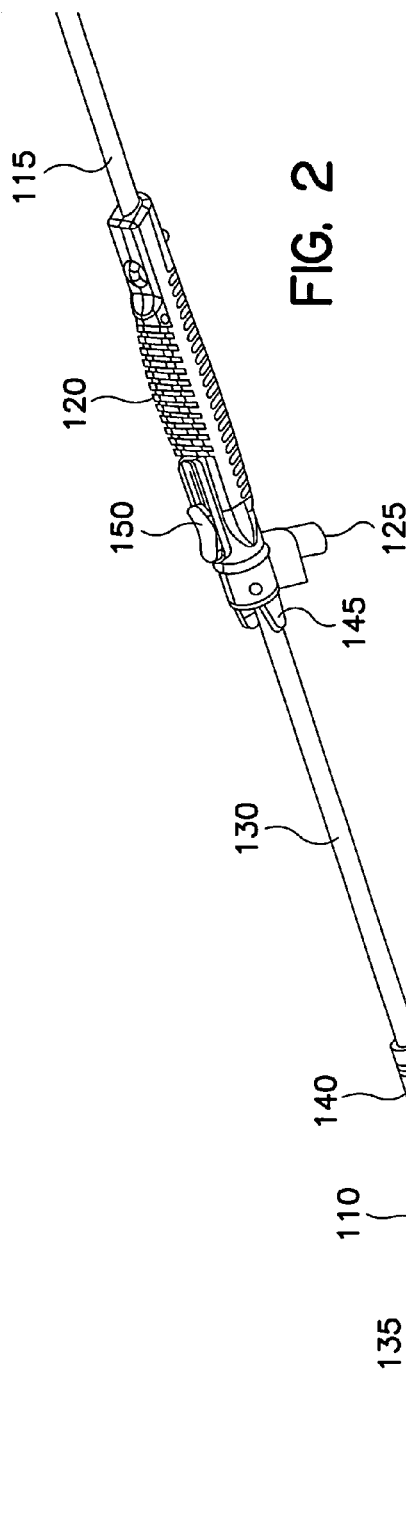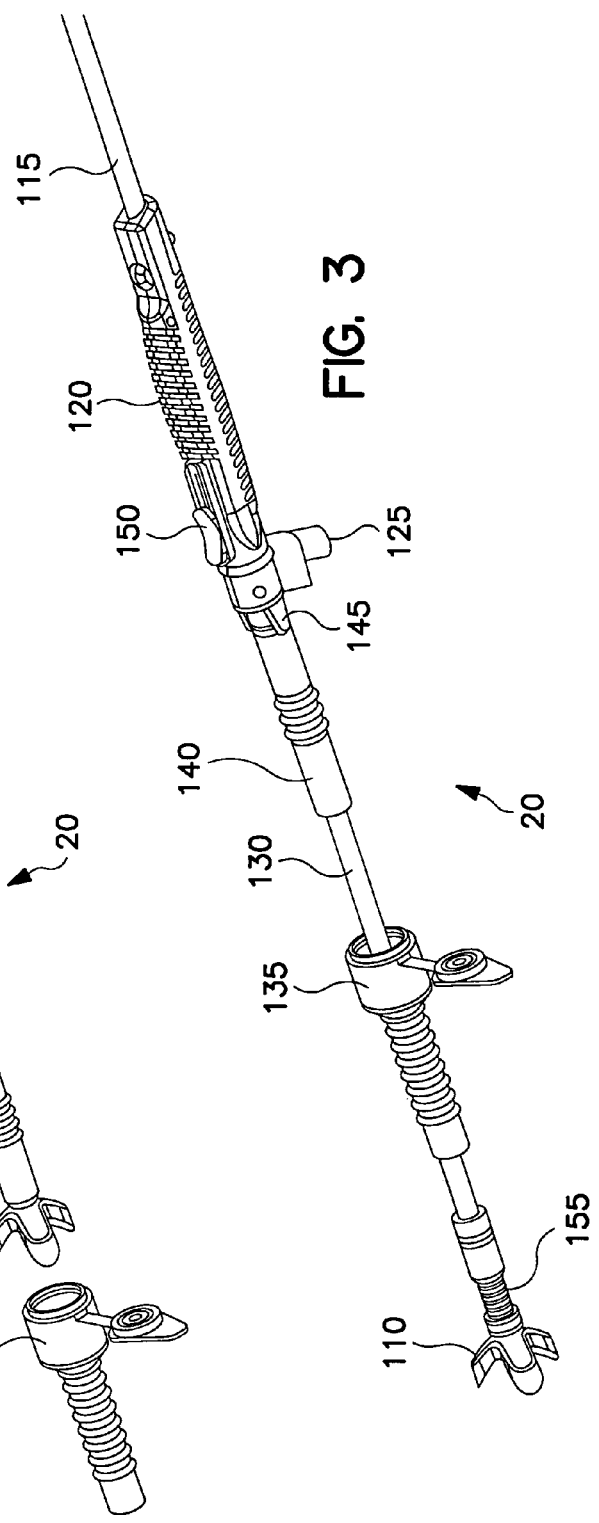

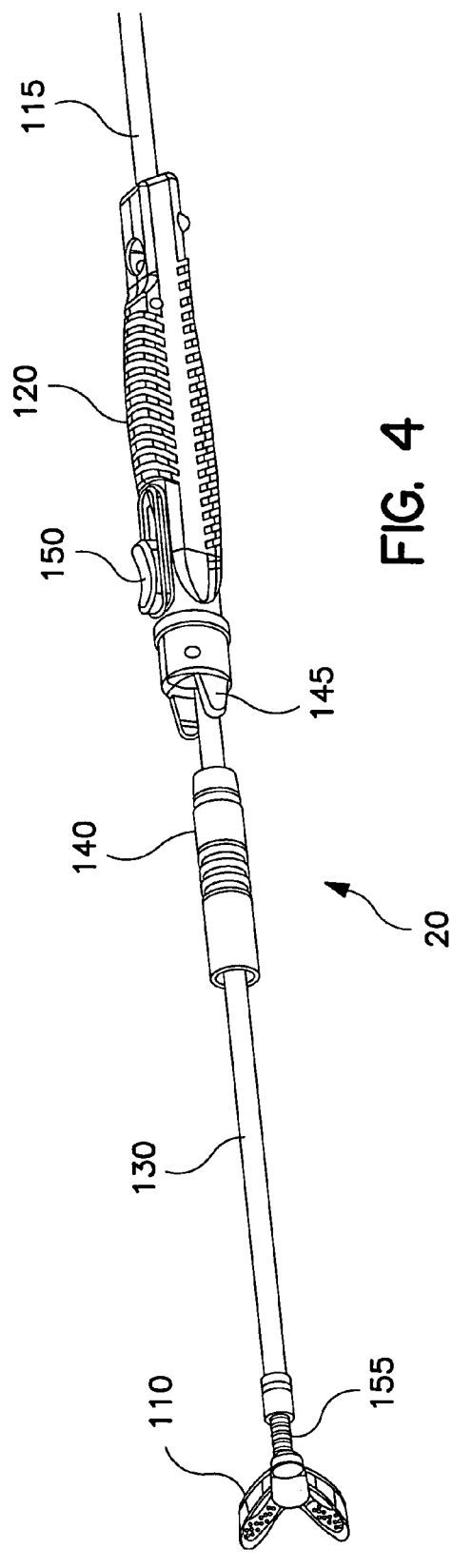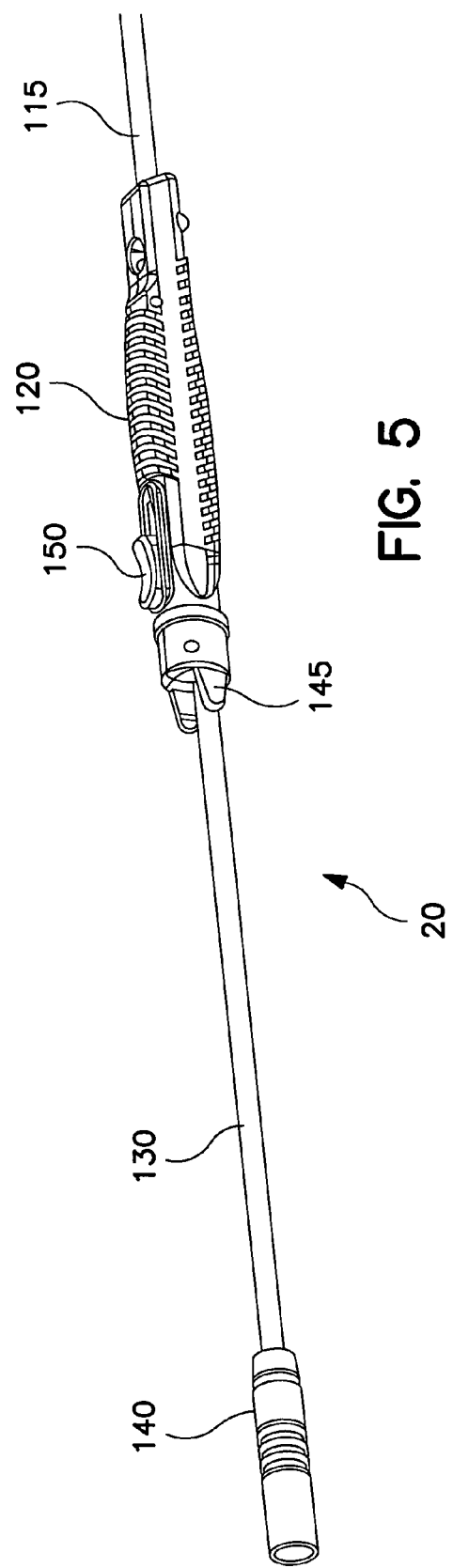

METHOD AND SYSTEM FOR ORGAN POSITIONING AND STABILIZATION

RELATED US APPLICATION DATA

This application claims the benefit of U.S. Provisional Application No. 60/404,969, filed Aug. 21, 2002, incorporated herein by reference in its entirety and of U.S. Provisional Patent Application 60/424,243, filed Nov. 6, 2002, incorporated herein by reference in its entirety.

FIELD OF THE INVENTION

This invention relates generally to a device, method and system for positioning an organ, and more particularly capable of positioning, manipulating, stabilizing and/or holding a heart during cardiac surgery.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, an alternative is to perform a coronary artery bypass graft (CABG) procedure. CABG surgery, also known as "heart bypass" surgery, generally entails the use of a graft or conduit to bypass the coronary obstruction and, thereby provide blood flow to the downstream ischemic heart tissues. The procedure is generally lengthy, traumatic and subject to patient risk. Among the risk factors involved is the use of a cardiopulmonary bypass (CPB) circuit, also known as a "heart-lung machine", to both pump blood and oxygenate the blood so that the patient's heart may be stopped during the surgery, with its function performed by the CPB circuit.

Conventional CABG procedures are typically conducted on an arrested heart while the patient is on CPB. The CPB circuit provides continuous systemic blood circulation, while cardioplegic cardiac arrest enables meticulous anastomosis suturing in a bloodless, still operative field. In the majority of patients, obstructed coronary arteries are bypassed; for example, with an in situ internal mammary artery (IMA) or a reversed segment of saphenous vein harvested from a leg.

Segments of other suitable blood vessels may also be used for grafting depending on availability, size and quality. In general, the body hosts seven potential arterial conduits, the right and left IMAs, the radial arteries and three viceral arteries, one in the abdomen, and two in the lower abdominal wall, though the latter may be quite short and are generally of limited usefulness. The viceral arteries include the gastroepiploic artery and the splenic artery.

The left IMA is best used for bypass to the left anterior descending (LAD) coronary artery and its diagonal branches. Whereas, the right IMA may be used for bypass to selected vessels more posterior such as the distal right coronary artery (RCA). The right IMA may also be used for bypass to selected marginal branches of the left circumflex coronary artery. A segment of radial artery harvested from an arm is generally used to revascularize the posterior surface of the heart. The right gastroepiploic artery may be used to revascularize almost any artery on the surface of the heart. It is most commonly used for bypass to the distal RCA or the posterior descending coronary artery. In unusual circumstances the splenic artery is used to revascularize posterior coronary arteries, but it is long enough to reach the marginal branches of the circumflex coronary artery.

Surgeons will generally complete bypass grafts to the following coronary arteries in a patient undergoing multiple bypass surgery in roughly the following order: posterior descending coronary artery (PDA), RCA, obtuse marginal branch, circumflex coronary artery, diagonal branch, and LAD. More generally, surgeons will revascularize the three coronary systems in the following order: right, circumflex, and anterior descending. However, the order may vary depending on whether the procedure is performed on a beating heart or an arrested heart. For arrested heart, about 3 to 4 bypass grafts of which 1 to 3 are free grafts are generally performed per procedure. In contrast, about 2 to 3 bypass grafts of which 0 to 2 are free grafts are generally performed per beating heart procedure. In general, 1 free graft is used per beating heart procedure.

When a saphenous vein or other blood vessel is used as a free graft in a procedure, two anastomoses are performed; one to the diseased artery distal to the obstruction (outflow end), and one proximally to the blood vessel supplying the arterial blood (inflow end). These anastomoses are generally performed using end-to-side anastomotic techniques. Rarely an end-to-end anastomotic technique is used. When more than one graft is required in any of the three coronary systems for complete revascularization of the heart, sequential graft techniques may be used to conserve the amount of blood vessels required. Sequential graft techniques use proximal side-to-side anastomoses and an end-to-side anastomosis to complete the graft. For example, a common sequence used in the anterior descending coronary system is a side-to-side anastomosis of graft to the diagonal branch and an end-to-side anastomosis of graft to the LAD coronary artery. However, only a small percentage of anastomoses are side-to-side anastomoses.

The majority of surgeons will complete the distal anastomosis of a graft prior to completion of the proximal anastomosis. The small percentage of surgeons who do complete the proximal anastomosis first usually do so to allow antegrade perfusion of cardioplegic solution through the graft during revascularization. Construction of the distal anastomosis, e.g., a saphenous vein-coronary artery anastomosis, begins by first locating the target artery on the heart. Next, an incision is made through the epicardium and the myocardium to expose the artery. An arteriotomy is then made using a knife to incise the artery. The incision is then extended with a scissors. The length of the incision approximates the diameter of the saphenous vein, about 4 to 5 mm. The diameter of the target artery is generally 1.5 to 2.0 mm. Since, most surgeons currently feel the distal take-off angle should be 30 to 45 degrees, the distal end of the saphenous vein is usually beveled at about 30 to 45 degrees.

Currently, surgeons generally construct the anastomosis via a ten-stitch running suture using 7-0 polypropylene suture material. The ten-stitch anastomosis typically comprises five stitches around the heel of the graft and five stitches around the toe. The five stitches around the heel of the graft comprise two stitches to one side of the apex of the graft and the artery, a stitch through the apex and two stitches placed at the opposite side of the apex. The graft is generally held apart from the coronary artery while the stitches are constructed using a needle manipulated by a forceps. Suture loops are drawn up and the suture pulled straight through to eliminate purse-string effect. The five stitches around the toe of the graft also comprise two stitches to one side of the apex of the graft and the artery, a stitch through the apex and two stitches placed at the opposite side of the apex. Again, suture loops are drawn up and the suture pulled straight through to eliminate purse-string effect. The suture ends are then tied.

The proximal anastomosis of a saphenous vein graft to the aorta, i.e. an aortosaphenous vein anastomosis, is formed by first removing the pericardial layer that covers the aorta. An occluding or side-biting clamp may be placed on the aorta at the anastomosis site or an aortotomy occlusion device may be used following creation of the aortotomy. A small circular or elliptical portion of the ascending aorta is excised forming a small opening 4 to 5 mm in diameter, i.e. the aortotomy. An aortic punch typically facilitates this procedure. The opening for a right-sided graft is made anterior or to the right lateral side of the aorta, whereas an opening for a left-sided graft is made to the left lateral side of the aorta. If the graft is to supply blood to the right coronary artery, the opening is generally made proximal on the aorta. If the graft is to supply blood to the anterior descending coronary artery, the opening is generally made in the middle on the aorta. And, if the graft is to supply blood to the circumflex artery, the opening is generally made distal on the aorta. The right graft opening is placed slightly in the right of the anterior midpoint of the aorta and the left graft opening slightly to the left. The end of the saphenous vein is cut back longitudinally for a distance of approximately 1 cm. A vascular clamp is placed across the tip of the saphenous vein to flatten it, thereby exposing the apex of the vein. Five suture loops of a running suture using 5-0 polypropylene are then placed around the 'heel' of the graft and passed through the aortic wall. Two stitches are placed on one side of the apex, the third stitch is placed precisely through the apex of the incision in the saphenous vein, and the final two stitches are placed on the opposite side of the apex. Suture traction is used to help expose the edge of the aortic opening to ensure accurate needle placement. Stitches include about 3 to 5 mm of the aortic wall for adequate strength. Suture loops are then pulled up to approximate the vein graft to the aorta. The remaining stitches are placed in a cartwheel fashion around the aortic opening thereby completing the remainder of the anastomosis.

Left-sided grafts are oriented so the apex of the incision in the "heel" of the saphenous vein will face directly to the left side. The stitches are placed in a clockwise fashion around the heel of the graft and in a counterclockwise fashion around the aortic opening. Right-sided grafts are oriented in a caudal fashion. The stitches are placed in a counterclockwise fashion around the heel of the graft and in a clockwise fashion around the aortic opening. Five suture loops complete the heel portion of the graft and an additional five or six may be used to complete the toe of the graft. Finished proximal anastomoses typically have a "cobra-head" appearance.

The surgeon takes steps to minimize the possibility of thrombosis, narrowing and/or premature closure of the anastomosis due to technical errors. Some surgeons feel the proximal anastomosis must have a take-off angle of 45 degrees while other surgeons believe the take-off angle is not critical. In addition, it was felt that intima-to-intima contact of the vessels at the anastomosis was critical for endothelization to occur, thereby making an ideal union of the vessels. However, most surgeons now feel intima-to-adventitia contact is acceptable. The main objective of the surgeon is to create an anastomosis with an expected long-term patency rate of greater than 5 to 10 years. The creation of an anastomosis currently takes approximately 10-15 minutes.

An important consideration for creating an anastomosis without error is adequate exposure of the target vessel. Acute visualization of the vessel walls is mandatory in order to properly place each stitch and avoid inadvertently including the back wall of the vessel in a stitch, which in effect narrows or completely occludes the vessel. In order to achieve the required exposure most surgeons will employee blood-less field devices such as shunts, snares, and misted blowers. Further, largely invasive surgical techniques are also employed to help the surgeon gain access to the grafting site. For this reason, CABG surgery is typically performed through a median sternotomy, which provides access to the heart and to all major coronary branches. A median sternotomy incision begins just below the sternal notch and extends slightly below the xiphoid process. A sternal retractor is used to spread the left and right rib cage apart for optimal exposure of the heart. Hemostasis of the sternal edges is typically obtained using electrocautery with a ball-tip electrode and a thin layer of bone wax. The pericardial sac is opened thereby achieving direct access to the heart.

A blood vessel or vessels for use in the graft procedure are mobilized from the patient. This usually entails mobilizing either a mammary artery or a saphenous vein, although other graft vessels as discussed above may also be used. A heart-lung or cardiopulmonary bypass is performed. This usually entails arterial and venous cannulation, connecting the bloodstream to a heart-lung machine, cooling the body to about 32 degrees Celsius, cross clamping of the aorta and cardioplegic perfusion of the coronary arteries to arrest and cool the heart to about 4 degrees Celsius. A proximal anastomosis may be performed on partial bypass using a partial occluding aortic cross-clamp or side-clamp. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

Problems that may be associated with conventional CABG procedures with CPB include the initiation of a systemic inflammatory response due to the interactions of blood elements with the artificial material surfaces of the CPB circuit. Global (hypothermic) cardiac arrest may result in global myocardial ischemia and cross clamping the ascending aorta may contribute to the patient experiencing a post-operative stroke. In fact, recent studies have shown aortic clamping and manipulation may release atherosclerotic debris into the bloodstream, resulting in neurologic injury.

Currently, the golden standard for creation of a vascular anastomosis is manual suturing. Manual suturing may be used to attach vascular grafts (either autografts or prosthetic grafts) for coronary bypass, femoral-femoral bypass (to relieve inadequate circulation in the legs), and AV fistulas and/or shunts (access portals for repeated puncture applications such as kidney dialysis or diabetes). However, a number of cardiac surgical procedures, e.g., off-pump, beating heart CABG procedures, minimally invasive procedures and even totally endoscopic procedures with access through ports only, may require a variety of new anastomotic techniques. The ability of performing anastomoses with limited or no CPB support may increase the possibility of performing more CABG procedures using minimally invasive surgical techniques. Avoiding the use of cross clamps and CPB or dramatically reducing pump run and cross clamp times may effectively minimize post-operative complications. For this reason, there is an increasing need for easier, quicker, less damaging, but reliable automated, semi-automated, or at least facilitated methods to replace or enhance the normal process of a manually sutured vascular anastomosis.

The major objective of any CABG procedure is to perform a technically perfect anastomosis. However, creation of a technically perfect anastomosis is generally complex, tedious, time consuming and its success is highly dependent on a surgeon's skill level. Therefore, creation of vascular anastomoses without the need to perform delicate and intricate suture lines may enable surgeons to more quickly create simpler and effective anastomoses. Currently, there are a number of techniques or procedures being investigated for facilitating the process of forming an anastomosis including vascular clips or staplers, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques may include the use of various biomaterials and/or biocompatible agents.

In an effort to reduce or eliminate occlusive anastomosis time, various techniques or procedures are being investigated. These procedures include coronary shunting techniques, which enable manual suturing without time-constraint due to persistent distal perfusion, and accelerated tissue-bonding techniques, e.g., tissue adhesives and laser welding. Some nonocclusive anastomosis techniques being developed require apposition of the intima of the graft to the adventitia of the recipient artery.

Sealants, adhesives or glues may be based on synthetic or biological substances or a combination of both. They are generally used to either seal post-operative internal air or fluid leaks, or to close a topical wound. Surgical sealants are generally absorbable materials used primarily to control internal bleeding and to seal tissue. Surgical adhesives, stronger than sealants, are often non-absorbable, but tend to be biologically based. Surgical glues, stronger than adhesives, are often synthetic and non-absorbable. In addition, glues are often used for topical wounds. Surgical glues are typically made from cyanoacrylates, a strong adhesive found in commercially available super glues. Biologically based sealants, adhesives or glues are generally derived from blood clotting components such as proteins (e.g., fibrinogen or fibrin), enzymes (e.g., thrombin) and/or platelets. Fibrin based sealants, adhesives or glues generally combine the protein fibrinogen with the enzyme thrombin to immediately begin the clotting process. One surgical adhesive currently being marketed includes a combination of collagen (proteins which form fibers to support body tissues), formalin (a form of formaldehyde), resorcinol and glutaraldehyde. Some sealants, adhesives or glues may be used to control bleeding or to reinforce suture or staple lines rather than to make tissues adhere, thus functioning more as hemostatic agents than glues.

There are a number of uses for sealants, adhesives or glues such as replacement for sutures and staples in minimally invasive procedures where the surgeon has little room to maneuver or for the repair of aortic dissections, where the tissue is so thin it may be damaged by sutures. They may also be used for anastomotic sealing, in which the seal should not be absorbed or carotid patching, where a complete seal is desired.

Laser welding is another potential method for forming an anastomosis. Laser welding uses lasers such as $CO_2$ lasers, argon lasers or Neodymium-YAG lasers, to join tissues together thermally instead of, for example, mechanically. One possible mechanism of laser welding of tissues is the thermal denaturation and coagulation of collagen fibrils in the tissue, which generally occur above 60° C. To improve the procedure, photosensitive dyes (e.g., indocyanine green) may be applied at the weld site to enhance light absorption and minimize thermal damage to the surrounding tissue. Using a dye that adsorbs light at a very specific frequency, a laser can be then used to selectively heat the dye and not the surrounding tissue. Photosensitive dyes used in laser welding procedures may or may not bind chemically to the tissue's proteins. Unlike sutures or staples, laser welding may offer a watertight seal to hold bodily fluids in, thereby preventing blood loss, infections and repeat surgeries. A further enhancement to the laser welding technique is to use a "solder". Solders may comprise synthetic and/or biological components. For example, proteins such as albumin have been used in various solder formulations. Typical laser welding devices include one or more flexible optical fibers and solder-delivery tubes that may be snaked through small ports or through a channel in an endoscope.

Mechanical anastomotic devices include stapling devices, clipping devices, ring and pin coupling devices and suturing devices. These anastomotic devices may be automated or semi-automated. Mechanical anastomotic devices also include mechanical couplers including stents, ferrules, and/ or rings. Materials used to form an anastomosis via a mechanical device and/or coupler may be biocompatible, bioabsorbable, bioactive and/or bioinert.

One-component intra-luminal mechanical anastomotic devices are generally stent-like in design. The graft and the target vessel, i.e., the aorta or coronary artery, are forced into tubular shapes by the device. In general, the application of this type of device is relatively easy. The device can be made to unfold by itself so no deformation forces are necessary at the anastomosis. In addition, angled anastomoses are possible. The device may however have a lot of foreign material exposed within the blood stream, thus increasing the risk of stenosis and thrombosis. In some cases, the device may prevent direct contact between the graft and the target vessel, thereby preventing the vessel walls from healing together. Intimal damage to both the graft and the target vessel may also occur during delivery of the device. Extra sealing methods, e.g., tissue sealants, may be needed to provide a leak-free anastomosis. In addition, the size of the device is strongly related to the size of the vessels. Therefore, a range of devices and measurement of the vessels may be needed.

Two component intra-luminal mechanical anastomotic devices require both the graft and the target vessel to be connected to their own coupling component, after which the two coupling components are connected to each other, thereby forming the complete anastomosis. Problems associated with construction of an anastomosis using a two component intra-luminal mechanical coupling device include mounting of the vessels and connection of the components. Tools for mounting the individual coupling components to each vessel and tools for connecting the coupling components together are both required.

One-component extra-luminal mechanical anastomotic devices generally require a delivery tool to position the coupling device in the recipient vessel. One component extra-luminal mechanical coupling devices generally allow direct intima-to-intima contact. In addition, this type of device will have less foreign material in the blood stream, thereby decreasing the risk of stenosis and thrombosis. For this reason, less biological testing may be required as opposed to an intra-luminal stent-like device. However, mounting of the graft to the coupling device may not be easy. Damage may occur due to everting of the graft onto the device. For example, everting of a graft onto a device may cause damage to the intimal layer. This damage may occur for two reasons: 1) solid grabbing of the vessel wall to evert an artery, thus one tip of the pair of pincers will roughly touch the intima; and, 2) eversion causes high strain (stretching), which will damage the arteries. Another problem is that skills are important for proper eversion. The surgeon has to estimate where to grab the vessel wall and how to lift it over one of the pins to obtain a symmetrical anastomosis. A specially designed mounting tool may make the step of mounting the graft onto the coupling device easier and may help to minimize damage to the graft. In addition, care must be taken to avoid compression of tissue by the coupling device since compression can cause pressure necrosis.

Two component extra-luminal mechanical anastomotic devices, like the two component intra-luminal mechanical coupling devices, require both the graft and the target vessel to be connected to their own coupling component, after which the two coupling components are connected to each other, thereby forming the complete anastomosis. Problems associated with construction of an anastomosis using a two component extra-luminal mechanical coupling device also include mounting of the vessels and connection of the components. Tools for mounting the individual coupling components to each vessel and tools for connecting the coupling components together may be required.

Hybrid anastomosis techniques combine one or more techniques, e.g., sutures or clips with glues or laser welding. A specific example of a hybrid anastomotic technique is the use of an intraluminal stent like device combined with an extraluminal application of biological glue.

One area that may create difficulties for the patient and extra expense and time for a stopped heart CABG procedure involves CPB. In a CPB procedure all the patient's blood, which normally returns to the right atrium, is diverted to a system that supplies oxygen to the blood and removes carbon dioxide from the blood and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1-9, immobilized the area of the bypass graft by encircling sutures deep enough to incorporate enough muscle to suspend an area of the heart and prevent damage to the coronary artery. More recently, Fanning et al. in "Reoperative Coronary Artery Bypass Grafting Without Cardiopulmonary Bypass", Annals Thorac. Surg. Vol. 55, (February 1993) pgs. 486-489 also reported immobilizing the area of the bypass graft with stabilization sutures.

Suction stabilization systems, such as the Medtronic Octopus® Tissue Stabilizer and Accessories (available from Medtronic, Inc., Minneapolis, Minn. USA), the current model being designated the "Octopus 4™ stabilization system", use suction to grip and immobilize the surface of the heart. Additionally, the system allows the surgeon to manipulate the anastomosis site into better view by rotating and supporting the heart. See, also, e.g., U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. The Octopus™ stabilizer facilitates moving or repositioning the heart to achieve better access to areas which would otherwise be difficult to access, such as the posterior or backside of the heart.

SUMMARY OF THE INVENTION

The present invention provides a device and system for positioning, manipulating, holding, grasping, immobilizing and/or stabilizing an organ, such as a heart. The system may include one or more tissue-engaging devices, one or more suction sources, one or more fluid sources, one or more energy sources, one or more sensors and one or more processors. The system may also include an indifferent electrode, a drug delivery device and/or an illumination device. A tissue-engaging device of the system may comprise a tissue-engaging head, a shaft and a handle. A support apparatus and a clamping mechanism for attaching the tissue-engaging device to a stable object, such as an operating table may also be used.

In one aspect of the invention a heart positioning device comprises a resiliently flexible suction head that flexes to conform to the surface of the heart, the suction head having a vacuum passageway in fluid communication with the head to apply suction between the head and the surface of the heart. A shaft having a vacuum lumen extending through the shaft is coupled at a distal end to the suction head. A handle is coupled to a proximal end of the shaft for remote manipulation of the position of the suction head. Means are provided for remotely changing the position of the head from a first position axially aligned with the shaft to a second, unaligned position.

In another aspect of the invention, the heart positioning device includes a sleeve slideably positioned on the shaft and sized to receive the suction head in a compressed condition such that the sleeve may be slideably advanced over the shaft to capture the suction head at the distal end thereof.

In yet another aspect of the invention, the sleeve can be slideably positioned on the shaft such that the suction head may be advanced or retracted with respect to the sleeve by manipulation of the handle. The sleeve can be configured to be used with port extending through an incision into the chest cavity of a patient or in place of the port by placing the sleeve into the incision.

In yet another aspect of the invention, a method of performing a surgical procedure on a heart may comprise providing a heart positioning device, introducing the suction head of the positioning device into a chest cavity of a patient through an incision; remotely changing the position of the suction head from a first position axially aligned with the shaft to a second, unaligned position while the suction head is within the chest cavity, engaging the heart with the suction head, positioning the heart into a non-physiological orientation; and performing a surgical procedure on the heart.

In yet another aspect of the invention, a method of performing a surgical procedure on a heart may comprise advancing a sleeve along the shaft of the heart positioning device to receive the suction head in a compressed condition, introducing the sleeve and compressed suction head of the positioning device into an incision extending into a chest cavity of a patient; and advancing the suction head from the sleeve such that it achieves an uncompressed condition inside the chest cavity of the patient.

In yet another aspect of the invention, a method of performing a surgical procedure on a heart may comprise advancing a sleeve along the shaft of the heart positioning device to receive the suction head in a compressed condition, introducing the sleeve and compressed suction head of the positioning device at least partially into a port extending into a chest cavity of a patient and advancing the suction head from the sleeve into the port and into the chest cavity such that it achieves an uncompressed condition.

In yet another aspect of the invention, a system for performing a medical procedure may comprise a resiliently flexible suction head that flexes to conform to the surface of the heart, the suction head having a vacuum passageway in fluid communication with the head to apply suction between the head and the surface of the heart. A shaft having a vacuum lumen through the shaft is coupled at a distal end to the suction head such that the suction head can be remotely moved from a first position axially aligned with the shaft to a second, unaligned position. A handle is coupled to a proximal end of the shaft for remote manipulation of the position of the suction head. A port is adapted to receive the suction head with the suction head in a compressed condition when the suction head is in the first, axially aligned condition. A suction source is in fluid communication with the heart positioning device.

In yet another aspect of the invention, a system may comprise a port adapted to receive at least a portion of the sleeve and the suction head with the suction head in a compressed condition within the sleeve The foregoing, and other, features and advantages of the invention will become further apparent from the following detailed description of preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 2 is a perspective view of a tissue-engaging device embodiment and port with the tissue-engaging device disengaged from the port.

FIG. 3 is a perspective view of the tissue engaging device embodiment and port of FIG. 2 with the tissue-engaging device engaged through the port.

FIG. 4 is a perspective view of another tissue-engaging device embodiment with a sliding sleeve in a retracted position.

FIG. 5 is a perspective view of the tissue-engaging device embodiment of FIG. 4 with the sliding sleeve in an advanced position covering the suction head.

FIG. 7b is a perspective view of a support sleeve for the movable joint assembly of FIG. 7a.

FIG. 9b is a support sleeve for the movable joint assembly of FIG. 9a.

DETAILED DESCRIPTION OF PREFERRED EMBODIMENTS

Figure 1:
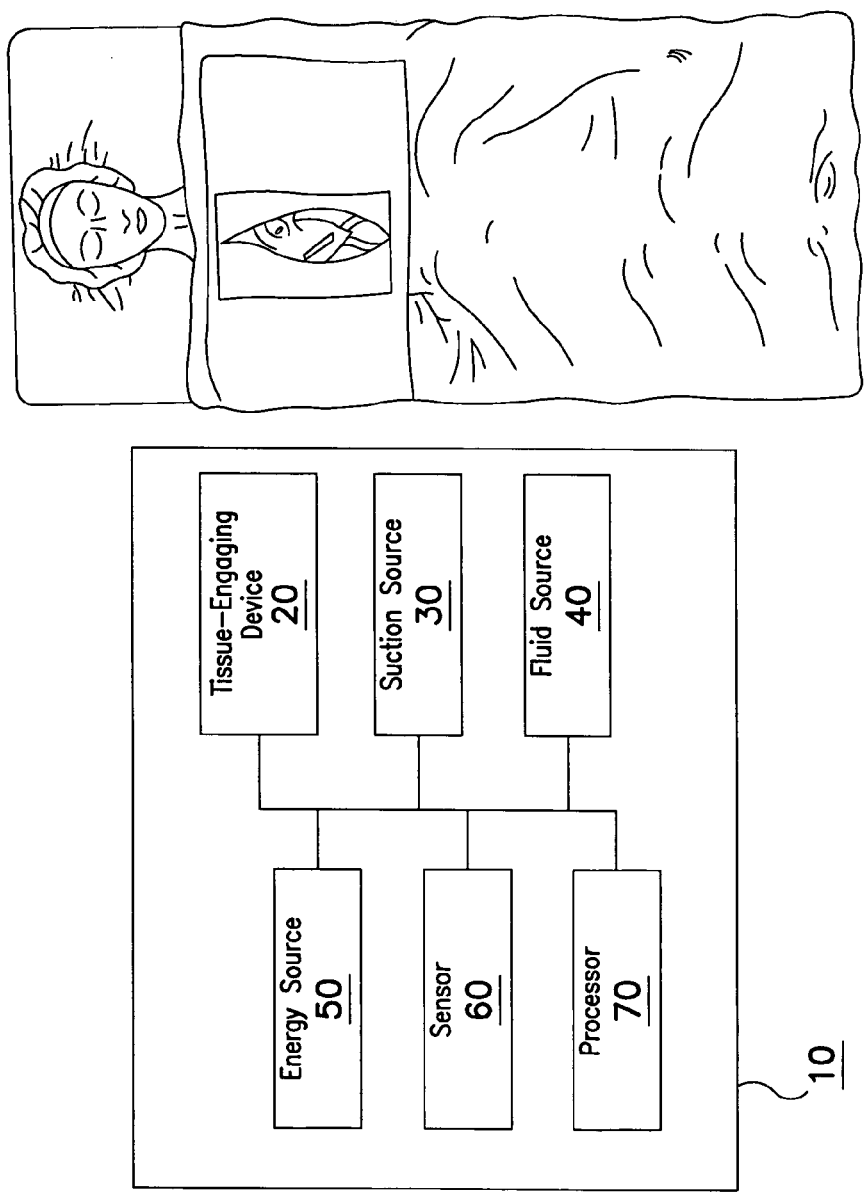
FIG. 1 is a schematic view of a system in accordance with the present invention.

FIG. 1 shows a schematic view of a system 10 for positioning, manipulating, holding, grasping, immobilizing and/or stabilizing tissue in accordance with the present invention. System 10 is shown to comprise tissue-engaging device 20, a suction source 30, a fluid source 40, an energy source 50, a sensor 60 and a processor 70. System 10 may also include an indifferent electrode, a drug delivery device and/or an illumination device. The indifferent electrode may be placed on the patient's body such as the back, thigh or shoulder or another site other than the suction site. The drug delivery device may be used to deliver drugs to a patient. The illumination device may be used to illuminate a surgical site.

As shown in FIGS. 2 and 3, the tissue-engaging device 20 may comprise a tissue-engaging head 110, a vacuum line 115, a handle 120, a shaft 130 coupled to the handle 120 and to the head 110 and a clamping point 125 for attaching device 20 to a stable structure, such as a rail attached to an operating table. At least one passageway through the shaft 130 and the handle 120 is in fluid communication with the suction source 30 via the vacuum line 115 such that vacuum is supplied to a suction port in the head 110. The tissue-engaging device 20 is sized to slideably fit within a cannula or port 135 by compressing the head 110 and sliding the port 135 over the head 110 and onto the shaft 130. The port 135 is used by placing it into a penetration into a body cavity of a patient such that the penetration is maintained in an open position with the port 135 projecting through the wall of the body cavity. The shaft 130 is in a sliding engagement through the center of the port 135 such that the head 110 can be advanced, retracted or rotated with the shaft 130 within the port 135. The shaft 130 transmits force applied by the operator onto the handle 120 to the head 110 such that it can manipulate tissue engaged by the head 110 in three dimensional space within the body cavity. As shown in FIG. 1, the tissue-engaging device 20 may also comprise one or more energy transfer elements, one or more connectors for connecting the one or more energy transfer elements to energy source 50, one or more sensing elements, one or more connectors for connecting the one or more sensing elements to sensor 60, one or more suction openings, one or more conduits for providing suction from suction source 30 to the one or more suction openings, one or more fluid openings, one or more conduits for providing fluid from fluid source 40 to the one or more fluid openings, and/or one or more connectors for connecting one or more components of tissue-engaging device 20 to processor 70.

As shown in FIGS. 4 and 5, the device 20 can also include a sleeve 140 slideably received on shaft 130 such that it can slide distally to capture and compress the head 110 and then be withdrawn proximally. A retaining member 145 adjacent to the handle 120 or integral with the handle 120 can capture a portion of the sleeve 140 such that it is retained in the proximal position. The sleeve 140 is preferably used to compress the head 110 prior to advancing the head into the port 135, however, the sleeve may also be used in place of the port 135 by inserting the sleeve into a penetration into a body cavity and manipulating the device 20 from the handle 120 by sliding or rotating the shaft 130 within the sleeve 140. The handle 120 includes a switch that may be advanced and retracted on the handle 120 to cause the head 110 to be directed to an angular position with the shaft by means of a movable joint 155. When used with the port 135, the port 135 is preferably sized to receive at least a portion of the sleeve 140 within the port 135 at a proximal portion of the port 135 so as to promote alignment of the compressed head 110 with the bore of the port 135 for easy entry of the compressed head 110 into the bore of the port 135.

The tissue-engaging device 20 and its components are preferably made of one or more biocompatible materials. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make suction device 20 may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, dacron, minerals or ceramics such as hydroxapatite, epoxies, human or animal protein or tissue such as bone, skin, teeth, collagen, lamin in, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of tissue-engaging device 20 may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Figure 6B:
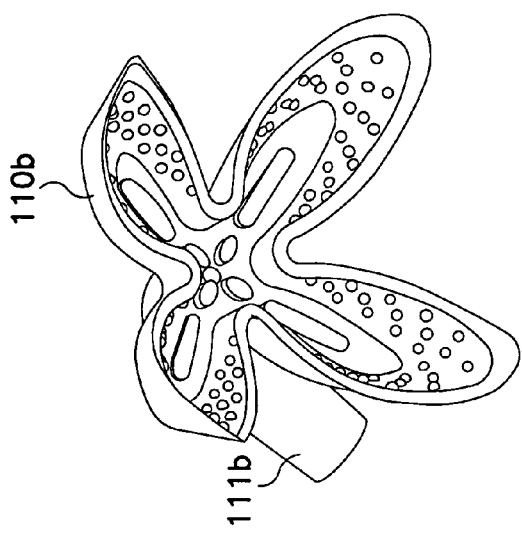
FIGS. 6a-f are views of alternative embodiments for suction heads for a tissue-engaging device.
Figure 6D:
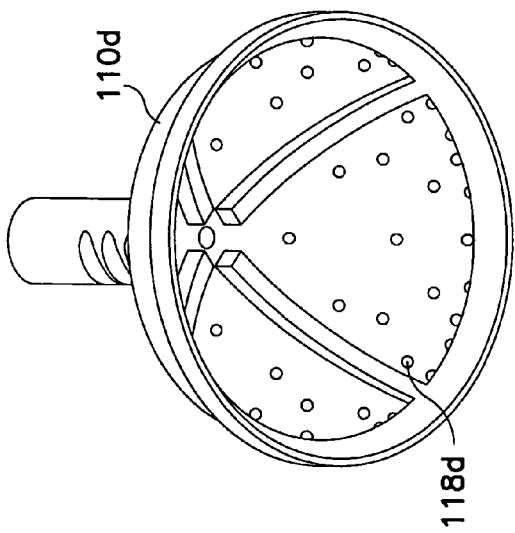
Figure 6A:
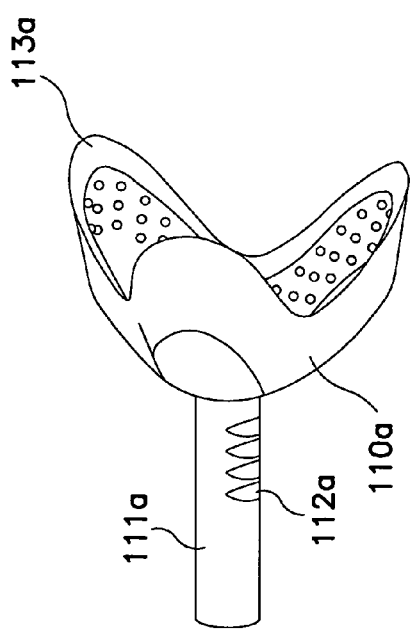
Figure 6C:
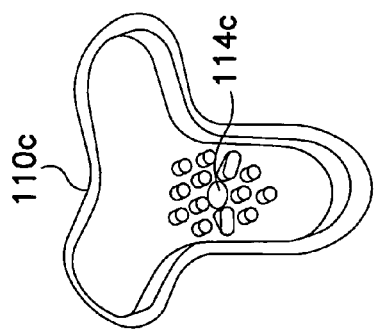
Figure 6F:
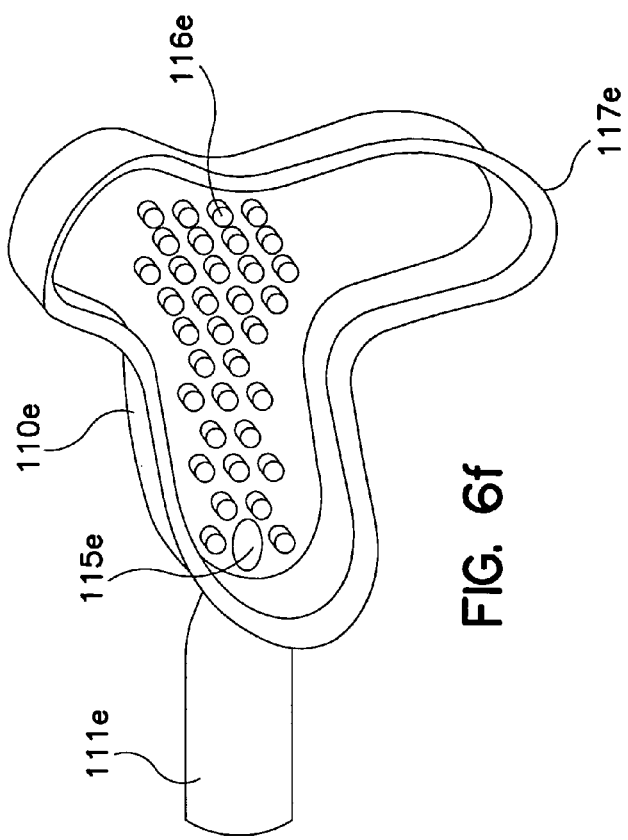
Figure 6E:
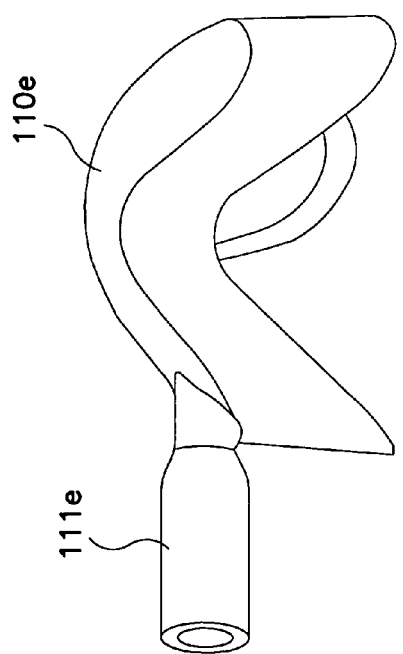
Figure 9A:
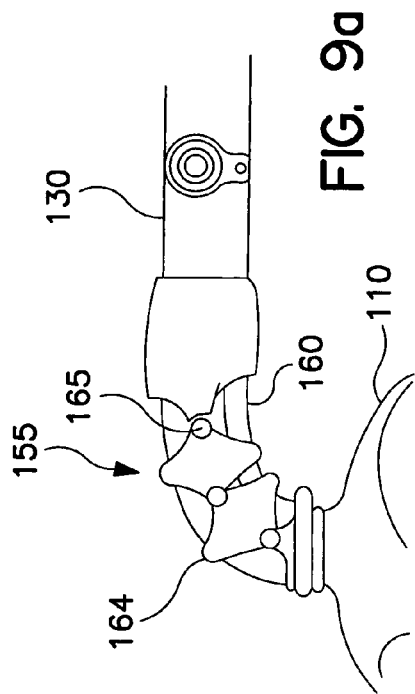
FIG. 9a is a side view of another movable joint assembly for a tissue-engaging device.
Figure 9B:
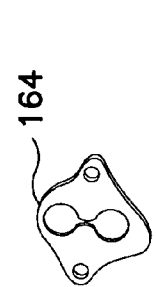

Referring now also to FIGS. 6a-f, tissue-engaging device 20 comprises a tissue-engaging head 110. The configuration of the head 110 can vary widely as depicted in embodiments 110a, 110b, 110c, 110d, and 110e. In FIG. 6a, head 110a is shown with a centrally located vacuum shaft 111a. Recesses 112a create points of weakness in the vacuum shaft 111a that allows the shaft to bend easily in the direction of the recesses without kinking the vacuum lumen inside the shaft 111a. Three lobes 113a extend from the shaft and are made from a resilient material such that the lobes can conform readily to a tissue surface. The lobes or legs of the tissue-engaging head may be arranged in starfish-shaped configuration. Preferably in this embodiment, there are 2-4 legs and, most preferably, there are 3 legs. The legs may be generally arcuate, curving downwardly away from the attached ends of the legs to the free ends of the legs. The legs may be sufficiently flexible that they may bend to conform to flat or curved surfaces, facilitating use of the tissue-engaging head at the apex or elsewhere on the heart. In one embodiment, the legs may be of differing sizes and/or shapes. Additional embodiments of such heads can be found in published patent application US 2002/0095139 A1, which is incorporated herein by reference in its entirety. FIG. 6b shows a four lobed head 110b with a vacuum shaft 111b angled from the central axis of the head 110b. FIG. 6c shows a head 110c with a vacuum port 114c, which is offset from the central axis of the head 110c. FIG. 6d shows a head 110d, which is not lobed but rather has a generally conical shape. FIGS. 6e-f show a head 110e having a vacuum shaft 111e extending to one of the lobes of the head 110e with a port 115e in one of the lobes which is in fluid communication with a lumen in the vacuum shaft. The tissue-engaging head is flexible to allow the head to conform to the surface of target tissue. The tissue-engaging head is also collapsible thereby allowing it to pass through a small incision and/or a surgical access port or cannula, e.g., an endoscopic port.

The tissue-engaging head of device 20 is preferably formed of medical grade silicone rubber or thermoplastic elastomeric material (e.g., polyurethane). Preferably, the material selected in this embodiment has a low durometer (e.g., about 50) so that the tissue-engaging head may conform to the surface of a heart of a patient. Also, the head is preferably resilient such that it can readily return to its original shape after being compressed within the aperture of a port or a sleeve. The material selected may be a substantially transparent or translucent material. Further contemplated are embodiments in which the tissue-engaging head is made of multiple materials of different durometers and properties, to form, for example, an endoskeleton or exoskeleton to provide varying degrees of stiffness and flexibility along different portions of the tissue-engaging head.

The tissue-engaging head 110 of device 20 may be coated with a lubricious coating or lubricant or it may be coated with paralyene. The tissue-engaging head may have a skirt or lip around its surface contacting area to help provide an airtight seal between the device and tissue.

The tissue-engaging head may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere. A tissue-engaging suction head is designed to engage or grasp tissue via suction. Each suction port, opening, orifice, channel or element may have a suction aperture coupling the port, opening, orifice, channel or element to a suction conduit, passageway or lumen. The suction aperture may be located in the center or at a position slightly off-center of the suction port, opening, orifice, channel or element. The suction aperture may be any shape including circular, oval, rectangular, or triangular. Each suction port, opening, orifice, channel or element may also be any suitable shape, for example circular, oval, rectangular, or triangular.

Preferably, each suction aperture would have a smaller diameter than the area of each suction port, opening, orifice, channel or element. A smaller diameter creates a high resistance pathway between the suction port, opening, orifice, channel or element and the suction conduit. Because of the high resistance pathway, loss of a tissue-to-port seal in one suction port (and thus loss of fixation of the suction port to the tissue) should not cause a precipitous pressure drop in the remainder of the suction ports.

Suction ports, openings, orifices, channels and/or elements may be arranged in any suitable fashion, such as a row or circle. In addition, the specific number of ports and their position may vary. Tissue-engaging head of device 20 may be covered with a removable covering during insertion into a patient's body to prevent blood or tissue from clogging the suction openings, although this is not necessary. Such coverings may include coverings of biocompatible material that would cover the entire tissue-engaging head of device 20. Alternatively, coverings may be placed just over the ports, such as, for example, mesh coverings or ribbed coverings.

A flexible tissue-engaging head may help to seal the head against tissue thereby helping to maintain suction. A sufficiently flexible head may draw down toward the surface of the heart more than the surface of the heart is pulled up into the tissue-engaging head.

The tissue-engaging head may comprise one or more mechanical means for engaging and/or grasping tissue. For example, the tissue-engaging head may comprise one or more hooks, clamps, magnets, screws, barbs, sutures, straps, tethers and/or staples. The tissue-engaging head may comprise a cuff or basket-type device designed to fit completely or partially around an organ, e.g., a heart. The tissue-engaging head may comprise one or more chemical means for engaging and/or grasping tissue. For example, the tissue-engaging head may comprise tissue glue or adhesive. The tissue-engaging head may comprise one or more coupling means for engaging and/or grasping tissue. For example, a suction means in addition to a mechanical means may be used to engage or grasp tissue. A magnetic means may also be used to engage or grasp tissue.

The tissue-engaging head 110, as shown in FIG. 2, may comprise a plurality of legs or lobes that may flex to conform to the surface of the heart. In use, the legs may allow the tissue-engaging head to be oriented to avoid placement over particular features of the heart anatomy, such as the cardiac arteries, or to avoid conflict with other surgical devices, such as a heart stabilizer of the type sold under the trade designation "OCTOPUS" by Medtronic, Inc., Minneapolis, Minn., USA.

The tissue-engaging head of device 20 is sufficiently resiliently flexible that it may flex to allow it to be pushed through a small incision, cannula or port. Once inside the chest cavity, the flexible head will return to its original shape. For example, the legs may be configured and sufficiently flexible that they can be drawn against one another to a collapsed position for entering into a thoracic cavity through a small incision, cannula or port in endoscopic and/or closed chest surgery. In addition, to closed chest surgery, this invention is applicable to open chest/split sternum surgery, in particular open chest, beating heart surgery for repositioning the heart to improve access to various coronary arteries.

One or more suction ports, openings, orifices, channels and/or elements may be provided along a tissue contact surface or tissue-engaging face of suction head 110 in fluid communication with the legs to apply suction between the legs and the surface of the heart to grasp the surface. One or more suction ports, openings, orifices, channels and/or elements may be positioned in or on each leg.

As shown in FIG. 6f, one or more tissue-engaging members or standoffs 116e may be provided within the tissue-engaging head to prevent vacuum channels from being closed off as tissue and the suction head are drawn together to allow continued fluid communication along the vacuum channels. In addition, one or more tissue-engaging members may be provided adjacent the orifice of a vacuum passageway to prevent the orifice and tissue being drawn together to close the orifice, thereby maintaining fluid communication between the vacuum passageway and the vacuum channels. The tissue-engaging suction head 110e has resiliently flexible flange 117e, which resiliently deforms against heart tissue to form a seal to help maintain the vacuum in vacuum channel. The standoff or tissue-engaging member 116e limits how far suction head 110e may be pulled down toward the surface of the heart to maintain a vacuum channel. Alternatively or in addition to the standoffs, a porous screen, mesh and/or fabric may be used to prevent the orifice and tissue being drawn together to close the orifice, thereby maintaining fluid communication between the vacuum passageway and the vacuum channels. The screen, mesh and/or fabric may engage or contact tissue. The screen, mesh and/or fabric may be placed on top of the standoffs. The screen, mesh and/or fabric may comprise a number of materials including metallic, ceramic and/or polymeric materials. The screen, mesh and/or fabric may be made of a synthetic or natural material. For example, the mesh may be made of a medical grade Dacron material. The screen, mesh and/or fabric may comprise bumps. Alternatively or in addition to standoffs, a porous foam, e.g., a polymeric foam, or other porous material or materials may be used to prevent the orifice and tissue being drawn together to close the orifice, thereby maintaining fluid communication between the vacuum passageway and the vacuum channels.

The tissue-engaging members may be round or elongated having a direction of elongation extending generally radial with respect to an orifice. The end of each flange may be beveled that the laterally outward edge of each end extends further than the laterally inward edge of each end. The flange 117e may extend along substantially the entire periphery of suction head 110e, so that vacuum can be maintained in the area defined between the flange 117e, the body of suction head 110e and the surface of the heart.

The tissue-engaging head of the device 20 may comprise one or more bumps 118d as shown in FIG. 6d, for example, located on the inner surface. Most preferably, bumps are generally hemispherical convex structures forming an integral part of the inner surface of the head 110d and particularly on a peripheral flange. When suction is pulled through vacuum channel to the vacuum port, bumps are pulled against the surface of an organ as the head deforms against the surface of the organ, e.g., the epicardium of the heart. Bumps help retain suction head in place on the heart. Bumps may be arranged in an alternating pattern, aligned pattern or irregular pattern, for example. Textures other than bumps are also contemplated, such as dimples, spikes, ridges, grooves (e.g., microgrooves), roughened texture (e.g., micro-textured), surface grain, strips, ribs, channels, ruts, embedding or adhering abrasive particles in or on the surface, gluing or laminating the texture onto the surface, or other surface treatments, conditions or configurations that increase the grip of the inner surface of the tissue-engaging head on the epicardium. It is also contemplated that the other underside surfaces of the tissue-engaging head may be textured to increase surface area and/or gripping. For example, a texture is preferably provided on the tissue-engaging members or standoffs, and this texture may be in the same form as the texture on the inner surface of the peripheral flange or a different gripping texture. The texture may be formed by any suitable methods, such as by molding, chemical etching, roughening with sandpaper or other abrasives (e.g., sand blasting), electrical means (such as EDM machining), thermal means, or laser etching, for example.

The tissue-engaging head 110 may include a tube fitting or lumen having an approximately ninety-degree bend. Other tube fittings or lumens having other angles of bend are also contemplated. The tube fitting or receives a vacuum line. Tissue-engaging head 110 and tube fitting then may be free to rotate relative to the end of the shaft 130. A filter element may also be provided within the tube fitting. The filter element preferably includes a through bore. The tissue-engaging head preferably has a flexible neck region, which allows the tissue-engaging head to be flexed. The neck region can also have a pre-bent configuration, for example, a 90-degree bend.

The tissue-engaging device 20 may include one or more fluid openings for delivery and/or removal of one or more fluids. Tissue-engaging device 20 may include needles for injection of fluids, drugs and/or cells into organ tissue. Tissue-engaging device 20 may comprise one or more catheters or cannulae for blood removal or delivery into an organ, e.g., a heart. In the case of the heart, a cannula or catheter may be placed through the wall of the heart and into an interior chamber of the heart comprising blood, for example, into the left ventricle. Blood may be removed or delivered via a blood pump. For example, a tube fitting, which is in fluid communication with a catheter or cannula, may be attached to a CPB circuit or a cardiac assist circuit such as an LVAD circuit. Tissue-engaging device 20 may include one or more openings for delivery or removal of one or more gases including smoke evacuation.

The tissue-engaging head may be designed to be an implantable medical device. For example, following a medical procedure such as a CABG procedure the tissue-engaging head may be left within the patient, thereby providing benefit to the patient. The tissue-engaging head may be made of one or more biodegradable materials, thereby allowing the head to be absorbed by the patient over time. The tissue-engaging head may be inflatable or pressurized with gas or liquid, thereby allowing it to be easily collapsed or inflated. The tissue-engaging head may be illuminated either by a light source or it may be fluorescent. Tissue-engaging head may comprise a camera.

Figure 10:
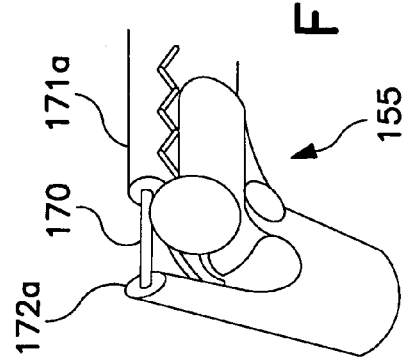
FIG. 10 is a side view of another movable joint assembly for a tissue-engaging device.
Figure 7A:
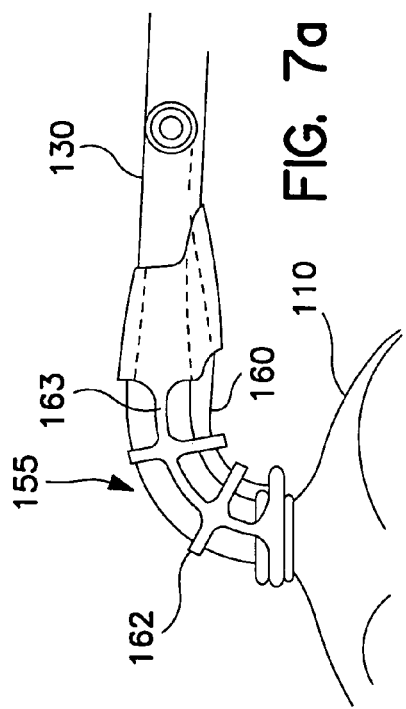
FIG. 7a is a side view of a movable joint assembly for a tissue-engaging device.
Figure 7B:
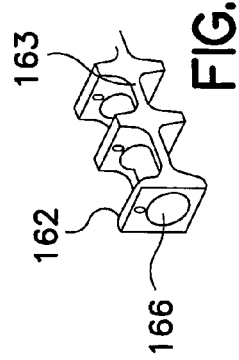
Figure 8:
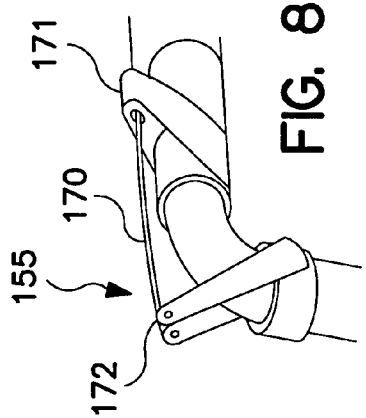
FIG. 8 is a side view of another movable joint assembly for a tissue-engaging device.

Tissue-engaging device 20 may comprise one or more maneuvering or support apparatus such as a shaft 130 or a handle 120 connected to the tissue-engaging head to position the head to thereby position or hold tissue. The support shaft or handle may be rigid, flexible, telescoping or articulating. The shaft or handle may comprise one or more hinges or joints for maneuvering and placing device 20 against tissue such as the heart such as the movable joint 155 shown in FIGS. 3 and 4. Referring now to FIGS. 7a-b and 9a-b, a movable joint can comprise one or more hinge or joint components that can be moved from a position that keeps the head in straight alignment with the longitudinal axis of the shaft to a bent position by means of a pull wire 160. Preferably, a bend of about 90 degrees can be achieved by use of the pull wire 160. Also preferably, the hinge or joint includes a resilient component such as a spring or a resilient material in the head 110 or shaft 120 or in a component joining the head and shaft that provides an opposing force tending to straighten the joint when tension on the pull wire 160 is released. The joint can be comprised of a single, bendable support member 162 with one or more longitudinally extending bendable members 163 or a series of support members 164 that are joined together at one or more pivot points 165. A ball and socket joint could also be used. Each of the support members 162, 164 include an aperture 165 through which tubing or other structure having a vacuum passage may provide a fluid connection between the head 110 and the suction source 30 through the shaft 130. The pull wire allows the movable joint 155 to be actuated remotely from outside the patient's body. Preferably, the pull wire 160 extends to the handle 120 where it can conveniently be operated from a button 150, knob, lever, trigger or other readily device readily manipulated by the operator. Also, preferably, the button 150 includes a means for locking the pull wire 160 in a retracted position such that the pull wire can remain in a retracted position until released by the operator. This releasable locking means can include a frictional or toothed engagement between the components of the handle 120 and the button 150. Also shown in FIGS. 8 and 10 are alternative devices in which stiff push wires 170 or other longitudinally stiff elements can be used to push the movable joint into place by advancing the push wire 170 through a guide lumen 171, 171a onto a distal bearing point 172, 172a, which forces the joint 155 to bend from a first position to a desired second position. Reversing the direction of travel for the push wire 170 can cause the joint 155 to return to its original position.

In alternative embodiments, the shaft or handle may be malleable or shapeable; the maneuvering or support means may be made of a shape memory alloy wherein heat may be use to change the shape of the maneuvering or supporting means; the shaft may be round, square or have any other cross-sectional shape; the shaft may comprise one or more hinges or joints such as a ball and socket joint; the hinges or joints may be articulated or moved manually, remotely and/or robotically; he support shaft or handle may be of the type that can readily be changed between a flexible or articulating condition and a rigid condition.

In operation, the tissue-engaging device 20 is prepared for use by connecting the vacuum line 115 to a suction source 30. The sleeve 140 is advanced toward the distal end of the device until the head 110 is compressed to a smaller diameter within the sleeve 140. The head 110 of the tissue-engaging device 20 can then be introduced into the body of the patient through a small incision. A cannula or port 135 can be used or the sleeve itself can be inserted within the incision. If a port 135 is used, the sleeve 140 and head 110 are placed into the opening of the port and the head 110 is advanced into the port 135 by transferred it from the sleeve 140 into the aperture of the port 135 while the head 110 remains compressed. As the head 110 emerges from the port 135, it returns to its uncompressed condition and the shaft 130 is disposed slideably within the port 135. An appropriate lubricant may be used to facilitate this procedure. The sleeve 140 can then be withdrawn to a proximal position on the shaft 130. When in position within the patient's body, the position of the head 110 can then be changed, if desired, by moving it on the flexible joint 155 from the button 150 on the handle 120. The head 110 is then placed against the desired portion of tissue to be engaged and suction from the suction source 30 is applied to the tissue. Once the device 20 is secured to the tissue by means of the applied suction, the handle 120 can then be moved by the operator to advance or retract the shaft 130, to rotate the shaft 130 or to use the port as a pivot point for the shaft 130. The operator is thereby able to reposition the head 110 and the tissue engaged with the head 110. If a port is not used, the sleeve 140 can be inserted into the incision and used as a port to slideably receive the shaft 130 and to permit the same range of motion for the manipulation of the head 110 as if a port had been used.

Figure 12:
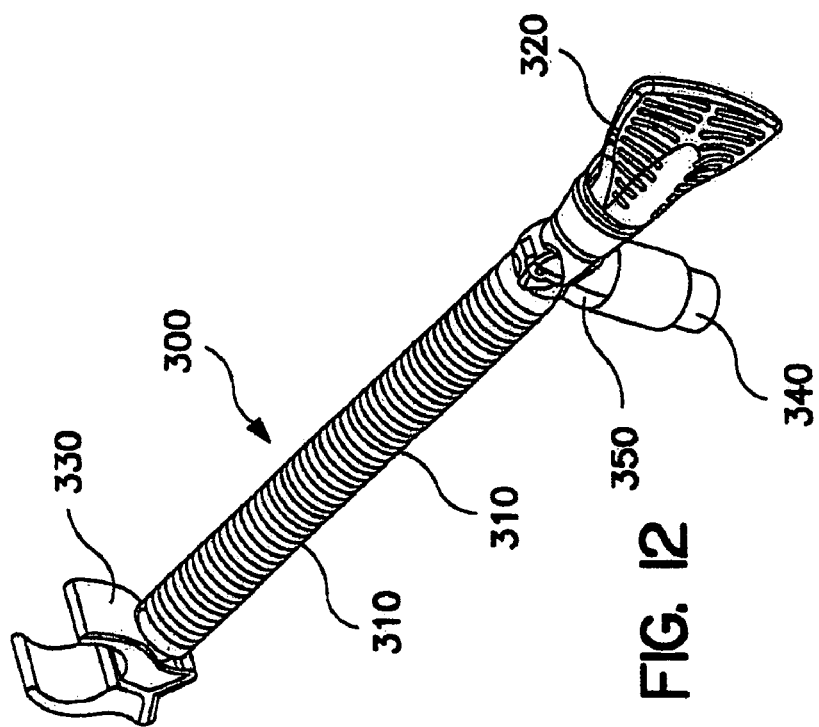
FIG. 12 is a perspective view of another support arm for a tissue-engaging device.
Figure 11:
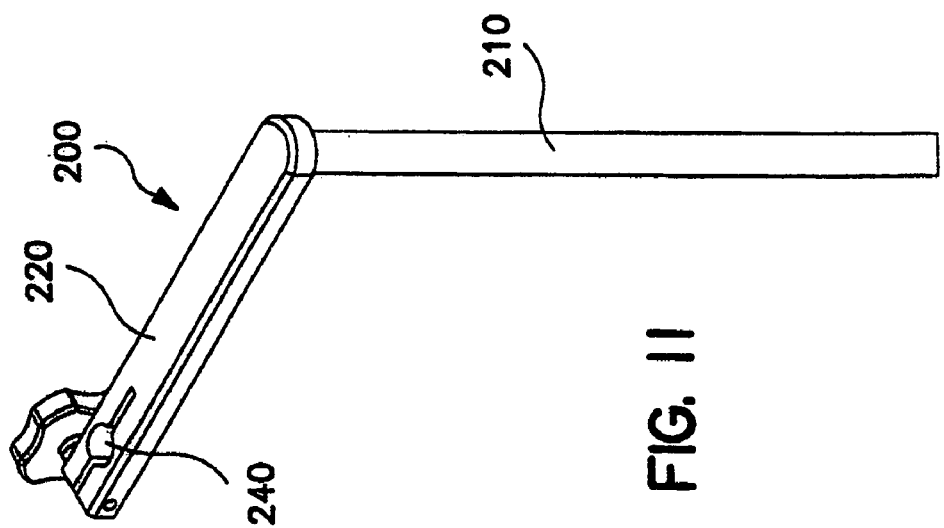
FIG. 11 is a perspective view of a support arm for a tissue-engaging device.
Figure 13:
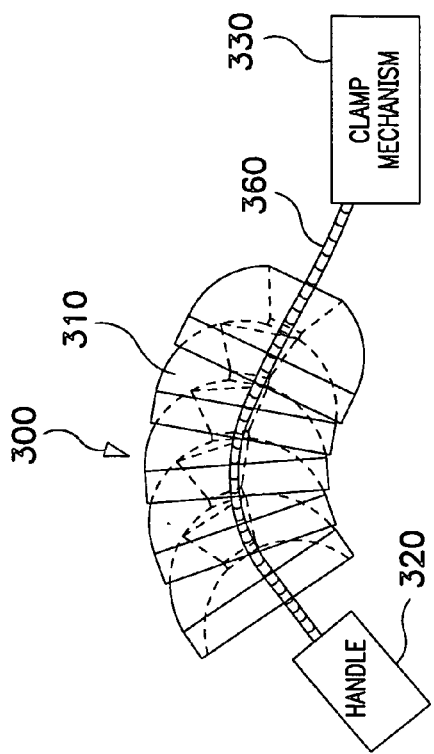
FIG. 13 is a schematic view of the operating components of the support arm of FIG. 12.

Referring now to FIGS. 11 and 12, the tissue-engaging device 20 can be secured to a table or other structure in the operating room by means of a bracket 200 as in FIG. 11 or by means of a support arm 300 as in FIG. 12. The purpose of the bracket and/or arm is to secure the tissue-engaging device 20 such that the tissue, once moved from its normal physiological position in the patient's body, may be held in place without requiring the operator to maintain the position of the device 20 manually. The bracket 200 includes an upright shaft 210 that is adapted to mate with holding devices on a stationary object such as an operating table. A horizontal bar 220 extends at an angle from the shaft 210 and includes at an end an aperture 240 that is adapted to receive a clamping point 125 of the tissue-engaging device 20 and a mechanism for clamping the clamping point 125 securely. A knob-activated screw mechanism is shown. The shaft 210 is long enough to permit the bar to extend over the body part of the patient to be treated as the patient rests on the operating table. The support arm 300 comprises a plurality of rigid members 310 that are free to articulate relative to one another until a central cable pulls the rigid members together in frictional engagement, which locks the support arm in a rigid condition. The cable is controlled, for example, by a handle 320 that may be rotated by the operator to pull tension on the cable, thereby drawing the rigid members together to lock them into position. As shown in FIG. 13, each rigid member has opposite ends, one of which is concave and the other of which is convex (e.g., hemispherical). The convex end of one rigid member fits into the concave end of the adjacent rigid member, and allows the member to articulate relative to the adjacent member if the central cable 360 has not been tensioned to lock the rigid members together. Most preferably, the rigid members are not of uniform cross section, with the rigid members closer to the distal end having a smaller cross section than the rigid members closer to the proximal end. A suitable articulating mechanism could be similar to the type used in the "OCTOPUS 3,"™ tissue stabilization system sold by Medtronic, Inc., Minneapolis, Minn. USA. Also, useful are the articulating arm mechanisms disclosed in U.S. Pat. Nos. 5,836, 311; 5,927,284 and 6,015,378, co-assigned U.S. patent application Ser. No. 09/396,047, filed Sep. 15, 1999; and Ser. No. 09/678,203, filed Oct. 2, 2000, and European Patent Publication No. EP 0 993 806, which are incorporated herein by reference in their entireties. The arm 300 may have near a proximal end a post 340 which can engage a stationary structure and secure the arm 300 in a relative stationary position. The post 340 can, for example be engaged with the aperture 240 of the bracket 200 of FIG. 11 and secured in position in order to ready it for use. The arm 300 can include at its distal end, a clamp 330 that can be secured about a portion of the tissue-engaging device 20 such as the shaft 130 or the handle 120. The clamp 330 is constructed to be capable of being tightened to hold the tissue-engaging device 20 and may be secured to the tissue-engaging device 20 either at the clamp 330 or remotely from the handle 320. Preferably, once the tissue-engaging device 20 has engaged the tissue and has been brought into a desired position by the operator, the clamp 330 is placed into engagement with a portion of the tissue-engaging device and the handle 320 is tightened to simultaneously tighten the clamp 330 about the tissue-engaging device and to tighten the rigid members 310 to a frictional engagement such that the arm 300 is rendered rigid and the tissue-engaging device 20 is held in a stationary position without further operator intervention. Once the surgical procedure is complete, the tissue-engaging device 20 can be disengaged from the tissue by releasing the tissue-engaging device 20 from the arm 300, re-positioning the tissue in a desired configuration by manipulation of the handle 120, and turning off the suction from the suction source 30. In order to provide additional range of motion for the device arm 300, a turret 350 can be provided near a proximal end of the arm 300. The turret 350 permits the arm 300 to be rotated with respect to the bracket 200. Preferably, the turret 350 can be locked by turning the handle 320 so that the clamp 330, rigid members 310 and turret 350 can be locked simultaneously.

Figure 14:
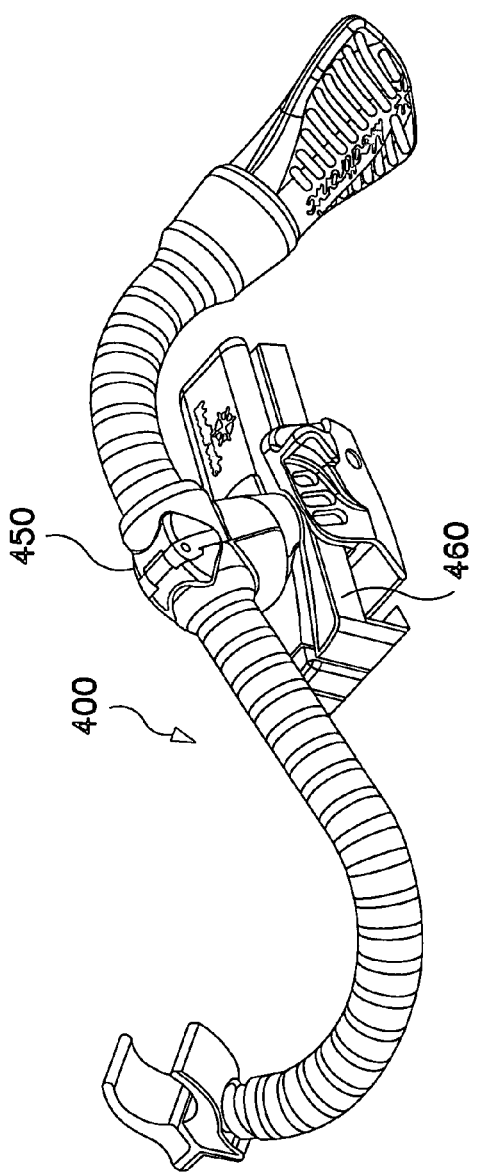
FIG. 14 is a perspective view of another support arm for a tissue-engaging device.
Figure 15:
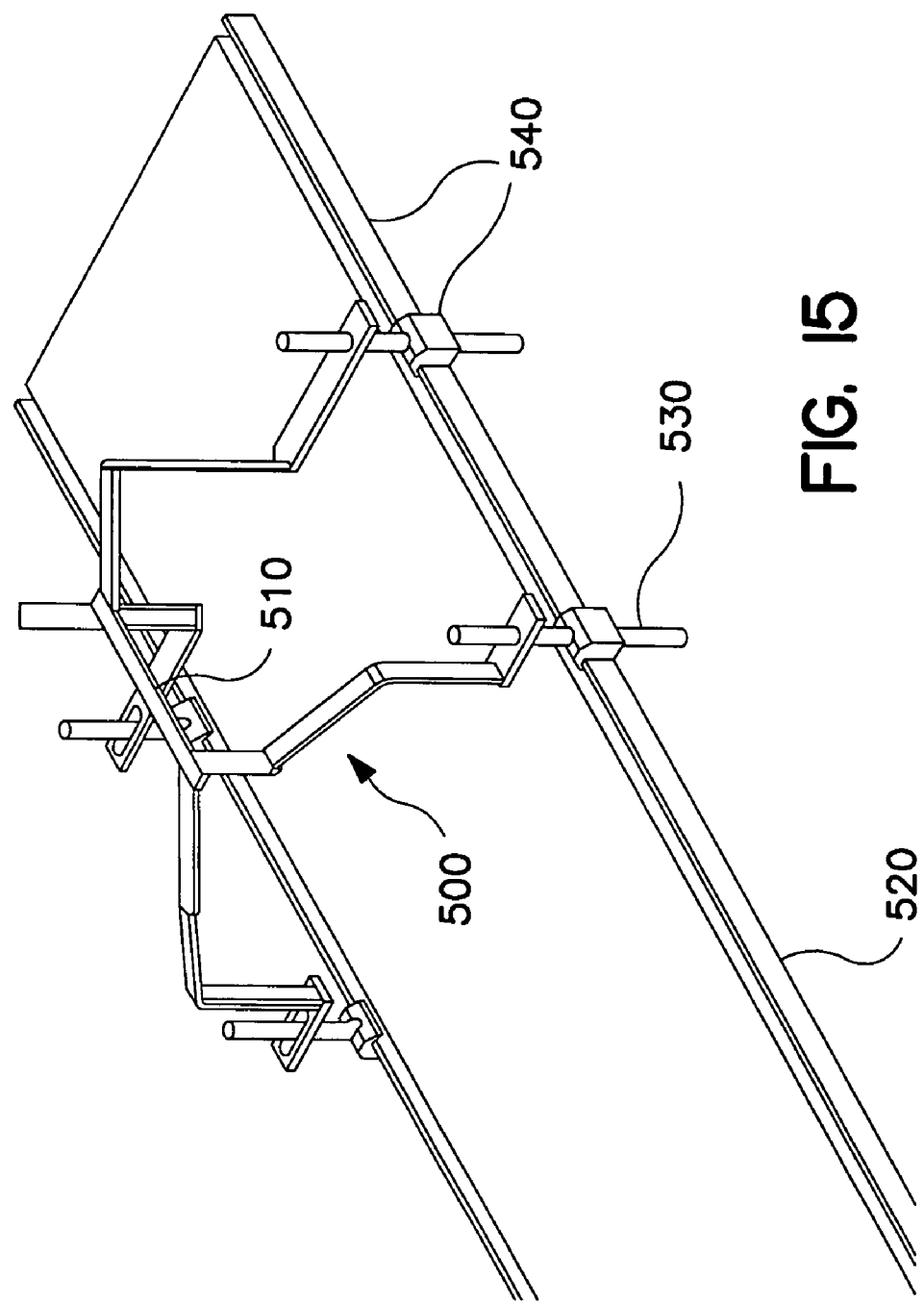
FIG. 15 is a perspective view of a system of support arms mounted to an operating table.

Referring now to FIGS. 14 and 15, an alternative embodiment to the arm and bracket embodiment of FIGS. 11 and 12 is shown for an arm 400 and bracket assembly 500. The arm 400 differs from the previously described embodiment in that a clamping mechanism 460 is fixed to the turret 450. The clamping mechanism 460 is adapted to be secured onto the flat portion 510 of the bracket assembly. Preferably, the clamping mechanism 460 can be a clamping mechanism as disclosed in U.S. patent application Ser. No. 10/122,971, filed Apr. 11, 2002, which is incorporated herein by reference in its entirety. Because the bracket assembly includes many flat portions 510 that are suitable for applying the clamping mechanism, the arm 400 can be applied at a variety of positions on the bracket assembly 500 depending on the needs of the surgeon to secure the tissue-engaging device 20 at a position that will preserve access the surgical site. The bracket assembly 500 may be attached to an operating table 520, thereby providing a stable platform. The bracket assembly 500 may be a fixed rail or a cage that wraps around the patient. The bracket assembly 500 may comprise one or more posts 530. More than one tissue-engaging device 20 may be coupled to the bracket assembly 500 as required by the surgical procedure. Clamping mechanisms 540 may be used to secure the bracket assembly 500 to the operating table 520 along a rail portion that allows the bracket assembly 500 to be positioned at an appropriate location with respect to the surgical site. The bracket assembly 500 is constructed to be adjustable to accommodate various sizes of patients and devices. The rail may be adjusted manually, remotely or robotically. Bracket assembly 500 hold sutures used during the surgical procedure. Specialized suture holding devices can be added to the bracket assembly 500 by means of clamps or built into the bracket assembly 500.

Figure 16:
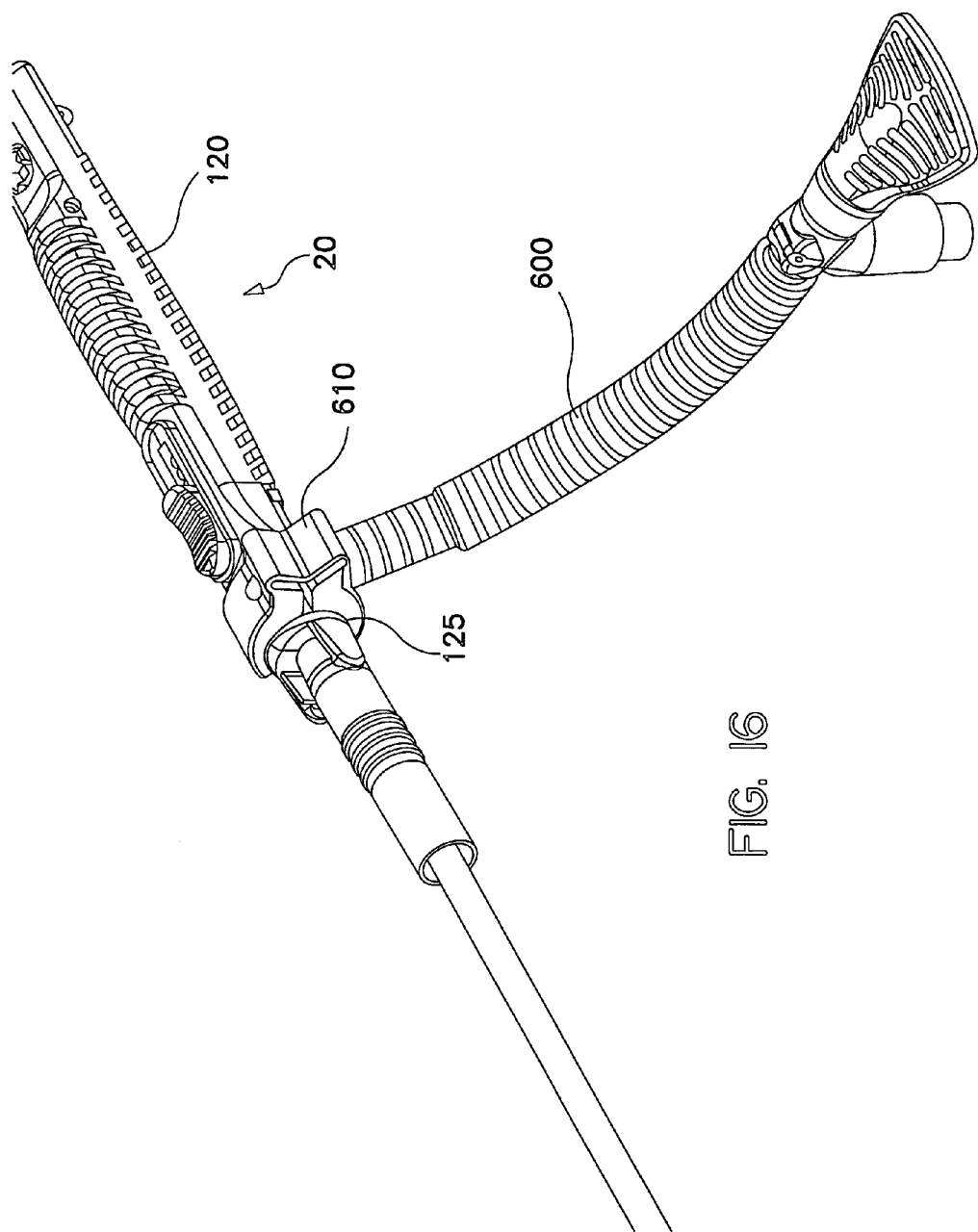
FIG. 16 is a partial perspective view of a tissue-engaging device coupled to a support arm.

Referring now to FIG. 16, an alternative embodiment of the arm 400 of FIG. 14 is shown as arm 600. Arm 600 includes a coupling 610 which can engage a clamping point 125 on the handle 120 to provide a positive lock of the arm 600 onto the handle 120. The clamping point 125 can include a release mechanism that allows the arm 600 to be releasably locked to the arm 600.

The tissue-engaging head 110 may comprise one or more energy transfer elements positioned on, along, within or adjacent a tissue contact surface. Energy transfer elements transfer energy to target tissue. For example, energy transfer elements may be conductive elements that may supply RF energy, microwave energy or ultrasound energy to target tissue. Energy transfer elements may be, for example, laser elements for supplying laser light to target tissue or they may be cryogenic elements. Two or more energy transfer elements or conductive elements of tissue-engaging device 20 may be arranged in a biopolar arrangement wherein at least one element is used as a positive electrode and at least one element is used as a negative electrode. One or more energy transfer elements or conductive elements of tissue-engaging device 20 may be arranged in a monopolar arrangement wherein at least one element is used as one electrode and an indifferent electrode is placed elsewhere on the patient's body such as the back, thigh or shoulder or another site other than the tissue-engaging device 20 site. Tissue-engaging head 110 may comprise electrodes that may be connected to energy source 50 via electrically conductive wires or leads. One or more electrodes may be positioned on one or more standoffs such as standoff 116e and/or the tissue-engaging head 110 may comprise a lead coupled to a perimeter electrode positioned on or along a flange such as flange 117e or a lead coupled to a conductive screen or mesh electrode.

Energy transfer elements or conductive elements may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, conductive metals, conductive polymers or plastics, and/or conductive ceramics. Energy transfer elements or conductive elements may not be conductive but may serve as a conduit to deliver a conductive material such as a conductive fluid. Energy transfer elements or conductive elements may be porous. For example, energy transfer elements or conductive elements may comprise porous polymers, metals, or ceramics. Energy transfer elements or conductive elements may be coated with non-stick coatings such as PTFE or other types of coatings as discussed herein. Energy transfer elements or conductive elements may be flexible thereby allowing them to conform to the surface of target tissue. Energy transfer elements or conductive elements may be malleable thereby allowing a surgeon to shape them to conform to the surface of target tissue.

Energy transfer elements or conductive elements may comprise one or more metal conductors such as windings inside a polymer or a conductive mesh material. The energy transfer elements or conductive elements may comprise tubes for delivering fluids. The tubes may comprise holes or slots. A polymer tube may be placed inside a metal tube to control fluid deliver through energy transfer elements or conductive elements. One or more of the energy transfer elements or conductive elements may be used as one or more nerve stimulation electrodes and/or as one or more cardiac stimulation electrodes. Electrodes may be used for cardiac pacing, defibrillation, cardioversion, sensing, stimulation, and/or mapping.

Energy transfer elements or conductive elements may comprise needles designed to penetrate tissues such as fat and muscle. For example, energy transfer elements or conductive elements may be designed to penetrate fat on the heart thereby allowing the energy transfer elements or conductive elements to reach cardiac tissue. The needles may allow fluids such as conductive fluids, chemicals such as tissue ablation chemicals, drugs, biological agents and/or cells to pass through. The needles may allow a vacuum or suction to pass through.

The tissue-engaging device 20 may also comprise one or more operator-controlled switches for regulation of tissue-engaging device 20 by the surgeon. The switch may be, for example, a hand switch, a foot switch, or a voice-activated switch comprising voice-recognition technologies. The switch may be physically wired to device 20 or it may be a remote control switch.

The tissue-engaging device 20 may be slaved to suction source 30, fluid source 40, energy source 50, sensor 60 and/or processor 70. For example, tissue-engaging device 20 may be designed to automatically stop engaging tissue when processor 70 sends a signal to stop tissue engagement. Tissue-engaging device 20 may include a visual and/or audible signal used to alert a surgeon to any change in tissue engagement and/or a visual and/or audible signal may be included in system 10. For example, a beeping tone or flashing light may be used to alert the surgeon when tissue-engaging device 20 has engaged tissue. Tissue-engaging device 20 may be slaved to a robotic system or a robotic system may be slaved to tissue-engaging device 20.

The tissue-engaging device 20 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. The tissue-engaging device 20 may be guided into a desired position using various guidance techniques, e.g., fluoroscopic guidance techniques.

The system 10 may include suction source 30 for providing suction to tissue-engaging device 20. As shown in FIG. 2, tissue-engaging device 20 may be attached to a flexible or rigid hose or tubing for supplying suction and/or fluids from a suitable suction source and/or fluid source to the target tissue surface through suction and/or fluid elements, openings, orifices, or ports of device 20. Tubing may comprise one or more stopcocks and/or connectors such as luer connectors. Suction may be provided to device 20 by the standard suction available in the operating room. Suction source 30 may be coupled to tissue-engaging device 20 with a buffer flask and/or filter. Suction may be provided at a negative pressure of between 200-600 mm Hg with 400 mm Hg preferred. As used herein, the terms "vacuum" or "suction" refer to negative pressure relative to atmospheric or environmental air pressure in the operating room. Alternatively, suction may be provided via one or more manual or electric pumps, syringes, suction or squeeze bulbs or other suction or vacuum producing means, devices or systems. Suction source 30 and/or tubing may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to device 20, thereby allowing device 20 to be easily manipulated by a surgeon. Another method that would allow the surgeon to easily manipulate device 20 includes incorporation of suction source 30 into device 20. For example, a small battery operated vacuum pump or squeeze bulb may be incorporated into device 20.

The system 10 may include fluid source 40 for providing fluids to tissue-engaging device 20. Tissue-engaging device 20 may be attached to a flexible or rigid hose or tubing for supplying fluids from fluid source 40 to the target tissue through fluid elements, openings, orifices, or ports of device 20. Fluid source 40 may be any suitable source of fluid. Fluid source 40 may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. Fluid source 40 may be powered by AC current, DC current, or it may be battery powered either by a disposable or re-chargeable battery. Fluid source 40 may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to device 20 to deliver fluid and/or remove fluid, thereby allowing device 20 to be easily manipulated by a surgeon. Fluid reservoirs may include an IV bag or bottle, for example. The fluid source 40 may also be incorporated into tissue-engaging device 20, thereby delivering fluid or removing fluid at the target tissue site. Fluid source 40 may be slaved to tissue-engaging device 20, suction source 30, energy source 50, sensor 60 and/or processor 70. For example, fluid source 40 may be designed to automatically stop or start the delivery of fluid while tissue-engaging device 20 is engaged with tissue. Fluid source 40 may be slaved to a robotic system or a robotic system may be slaved to fluid source 40. The fluid source 40 may comprise one or more switches, e.g., a surgeon-controlled switch. One or more switches may be incorporated in or on fluid source 40 or any other location easily and quickly accessed by the surgeon for regulation of fluid delivery by the surgeon. A switch may be, for example, a hand switch, a foot switch, or a voice-activated switch comprising voice-recognition technologies. A switch may be physically wired to fluid source 40 or it may be a remote control switch. Fluid source 40 and/or system 10 may include a visual and/or audible signal used to alert a surgeon to any change in the delivery of fluid. For example, a beeping tone or flashing light may be used to alert the surgeon that a change has occurred in the delivery of fluid. The fluids delivered to tissue-engaging device 20 may include saline, e.g., normal, hypotonic or hypertonic saline, Ringer's solution, ionic, contrast, blood, and/or energy-conducting liquids. An ionic fluid may electrically tissue-engaging device 20 to tissue thereby lowering the impedance at the target tissue site. An ionic irrigating fluid may create a larger effective electrode surface. An irrigating fluid may cool the surface of tissue thereby preventing over heating or cooking of tissue that can cause popping, desiccation, and charring of tissue. A hypotonic irrigating fluid may be used to electrically insulate a region of tissue. Fluids delivered to tissue-engaging device 20 may include gases, adhesive agents and/or release agents. Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with a fluid. Biological agents may be found in nature (naturally occurring) or may be chemically synthesized. Cells and cell components, e.g., mammalian and/or bacterial cells, may be delivered with a fluid.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

System 10 may include a drug delivery device. The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., fluoroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into tissue-engaging device 20, thereby delivering drugs at or adjacent the target tissue site or the drug delivery device may be placed or used at a location differing from the location of tissue-engaging device 20. For example, a drug delivery device may be placed in contact with the inside surface of a patient's heart while tissue-engaging device 20 is placed or used on the outside surface of the patient's heart. The drug delivery device may be slaved to tissue-engaging device 20, suction source 30, fluid source 40, energy source 50, sensor 60 and/or processor 70. For example, a drug delivery device may be designed to automatically stop or start the delivery of drugs during tissue engagement of tissue-engaging device 20. The drug delivery device may be slaved to a robotic system or a robotic system may be slaved to the drug delivery device. The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device and/or system 10 may include a visual and/or audible signal used to alert a surgeon to any change in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encamide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., fluoroscopic guidance and/or a guiding catheter or guide wire techniques. One catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage System 10 may include energy source 50. Energy source 50 may comprise a control unit. Tissue-engaging device 20 may be permanently or non-permanently attached to energy source 50. Energy source 50 may supply electrical energy, radiofrequency (RF) energy, laser energy, thermal energy, microwave energy, ultrasound energy and/or any other appropriate type of energy that may be used for the desired medical procedure, for example to ablate tissue. Energy source 50 may be powered by AC current, DC current or it may be battery powered either by a disposable or rechargeable battery. Energy source 50 may be used to coordinate the various elements of system 10. For example, energy source 50 may be configured to synchronize activation and deactivation of suction source 20 with the delivery of energy. Energy source 50 may incorporate a controller or processor. For example, the controller may process sensed information from a sensor. The controller may store and/or process such information before, during and/or after a medical procedure. For example, the patient's tissue temperature may be sensed, stored and processed prior to and during a medical procedure. Energy source 50 may be used to control the energy supplied to one or more energy transfer elements of tissue-engaging device 20. Energy source 50 may also gather and process information from one or more sensors. This information may be used to adjust energy levels and times. Energy source 50 may incorporate one or more switches to facilitate regulation of the various system components by the surgeon. One example of such a switch is a foot pedal. A switch may also be, for example, a hand switch, or a voice-activated switch comprising voice-recognition technologies. A switch may be physically wired to energy source 50 or it may be a remote control switch. A switch may be incorporated in or on one of the surgeon's instruments, such as surgical site retractor, e.g., a sternal or rib retractor, tissue-engaging device 20, or any other location easily and quickly accessed by the surgeon. Energy source 50 may also include a display. Energy source 50 may also include other means of indicating the status of various components to the surgeon such as a numerical display, gauges, a monitor display or audio feedback. Energy source 50 may incorporate a cardiac stimulator and/or cardiac monitor. For example, electrodes used to stimulate or monitor the heart may be incorporated into tissue-engaging device 20. Energy source 50 may comprise a surgeon-controlled switch for cardiac stimulation or monitoring, as discussed earlier. Cardiac stimulation may comprise cardiac pacing and/or cardiac defibrillation. Energy source 50 may incorporate a cardiac mapping device for mapping the electrical signals of the heart. A visual and/or audible signal used to alert a surgeon to the completion or resumption of energy delivery, suction, sensing, monitoring, stimulation and/or delivery of fluids, drugs and/or cells may be incorporated into energy source 50. For example, a beeping tone or flashing light that increases in frequency as the energy delivered increases.

System 10 may include sensor 60. Sensor 60 may be incorporated into tissue-engaging device 20 or it may be incorporated into a separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. Sensor 60 may comprise one or more switches, e.g., a surgeon-controlled switch. One or more switches may be incorporated in or on a sensor device or any other location easily and quickly accessed by the surgeon for regulation of sensor 60 by the surgeon. A switch may be, for example, a hand switch, a foot switch, or a voice-activated switch comprising voice-recognition technologies. A switch may be physically wired to sensor 60 or it may be a remote control switch. Sensor 60 may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed. Sensor 60 may comprise one or more temperature-sensitive elements, such as a thermocouple, to allow a surgeon to monitor temperature changes of a patient's tissue. Alternatively, sensor 60 may sense and/or monitor voltage, amperage, wattage and/or impedance. For example, an ECG sensor may allow a surgeon to monitor the hemodynamics of a patient during a heart positioning procedure. The heart may become hemodynamically compromised during positioning and while in a non-physiological position. Alternatively, sensor 60 may be any suitable blood gas sensor for measuring the concentration or saturation of a gas in the blood or tissues. For example, sensor 60 may be a sensor for measuring the concentration or saturation of oxygen or carbon dioxide in the blood or tissues. Alternatively, sensor 60 may be any suitable sensor for measuring blood pressure or flow, for example a Doppler ultrasound sensor system, or a sensor for measuring hematocrit (HCT) levels. Alternatively sensor 60 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity. Sensor 60 may be based on potentiometric technology or fiber optic technology. For example, the sensor may comprise a potentiometric or fiber optic transducer. An optical sensor may be based on either an absorbance or fluorescence measurement and may include an UV, a visible or an IR light source. Sensor 60 may be used to detect naturally detectable properties representative of one or more characteristics, e.g., chemical, physical, mechanical, thermal, electrical or physiological, of system 10 and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties of system 10 may include, for example, pressure, tension, stretch, fluid flow, electrical, mechanical, chemical and/or thermal. For example, sensor 60 may be used to sense, monitor and/or control suction or vacuum delivered from suction source 30. Sensor 60 may be used to measure suction between device 20 and tissue. Sensor 60 may be used to sense, monitor and/or control fluid delivered from fluid source 40. Sensor 60 may be used to sense, monitor and/or control energy delivered from energy source 50. Sensor 60 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor. Sensor 60 may be incorporated into tissue-engaging device 20 or sensor 60 may be placed or used at a location differing from the location of tissue-engaging device 20. For example, sensor 60 may be placed in contact with the inside surface of a patient's heart while tissue-engaging device 20 is placed or used on the outside surface of the patient's heart.

Tissue-engaging device 20, suction source 30, fluid source 40, energy source 50 and/or processor 70 may be slaved to sensor 60. For example, tissue-engaging device 20 may be designed to automatically adjust suction if sensor 60 measures a predetermined sensor value, e.g., a particular suction value. Sensor 60 may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

System 10 may include processor 70. Processor 70 may receive and preferably interpret the signal from sensor 60. Processor 70 may comprise software and/or hardware. Processor 70 may comprise fuzzy logic. A suitable amplifier may amplify signals from sensor 60 before reaching processor 70. The amplifier may be incorporated into processor 70. Alternatively the amplifier may be incorporated into sensor 60 or tissue-engaging device 20. Alternatively, the amplifier may be a separate device. Processor 70 may be a device separate from tissue-engaging device 20, suction source 30, fluid source 40, energy source 50 or sensor 60. Processor 70 may be incorporated into tissue-engaging device 20, suction source 30, fluid source 40, energy source 50 or sensor 60. Processor 70 may control the energy delivered from the energy source 50. For example, a signal of a first intensity from sensor 60 may indicate that the energy level from energy source 50 should be lowered; a signal of a different intensity may indicate that energy source 50 should be turned off. Preferably, processor 70 may be configured so that it may automatically raise or lower the suction delivered to device 20 from suction source 30, the fluids delivered to device 20 from fluid source 40 and/or the energy delivered to device 20 from energy source 50. Alternatively, the control of suction source 30, fluid source 40 and/or energy source 50 based on output from processor 70 may be manual. Processor 70 may include a visual display or monitor, such as, for example, a LCD or CRT monitor, to display various amounts and types of information. By software control, the user may choose to display the information in a number of ways. The monitor may show, for example, a currently sensed parameter, e.g., temperature. The monitor may also lock and display the maximum sensed value achieved. Sensed information may be displayed to the user in any suitable manner, such as for example, displaying a virtual representation of tissue-engaging device 20 on the monitor. Alternatively, the monitor may display the voltage corresponding to the signal emitted from sensor 60. This signal corresponds in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would turn off or adjust the energy source 50. The display of processor 70 may alternatively be located on tissue-engaging device 20, suction source 30, fluid source 40, energy source 50 and/or sensor 60. An indicator, such as an LED light, may be permanently or removeably incorporated into tissue-engaging device 20, suction source 30, fluid source 40, energy source 50 and/or sensor 60. The indicator may receive a signal from sensor 60 indicating that the tissue had reached an appropriate value, for example temperature. In response, the indicator may turn on, change color, grow brighter or change in any suitable manner to indicate that the flow of energy from energy source 50 should be modified or halted. The indicator may also be located on tissue-engaging device 20, suction source 30, fluid source 40, energy source 50, sensor 60 and/or may be located on another location visible to the user. Alternatively, the processor 70 may include an audio device that indicates to the user that the delivery of suction, fluids and/or energy should be halted or adjusted. Such an audio device may be, for example, a speaker that broadcasts a sound (for example, a beep) that increases in intensity, frequency or tone as a parameter sensed by sensor 60 increases. The user may adjust, for example, turn down or turn off energy source 50 when the sound emitted reaches a given volume or level. The audio device may also give an audible signal (such as the message "turn off energy source"), for example, when a parameter sensed by sensor 60 reaches a certain level. Such an audio device may be located on tissue-engaging device 20, suction source 30, fluid source 40, energy source 50 and/or sensor 60. The audio device may also be a separate device. Processor 70 may comprise one or more switches, e.g., a surgeon-controlled switch. One or more switches may be incorporated in or on processor 70 or any other location easily and quickly accessed by the surgeon for regulation of processor 70 by the surgeon. A switch may be, for example, a hand switch, a foot switch, or a voice-activated switch comprising voice-recognition technologies. A switch may be physically wired to processor 70 or it may be a remote control switch.

The system 10 may include an illumination device. The illumination device may comprise one or more light sources and/or illuminating materials, e.g., glow-in-the-dark materials. For example, the tissue-engaging head of device 20 may comprise one or more glow-in-the-dark materials. The illumination device may be based on fluorescence technologies. The illumination device may comprise fiber optic technologies; for example a fiber optic conduit may deliver light from a remote light source to an area adjacent tissue-engaging device 20 for illumination of a surgical site. The illumination device may comprise a light pipe, for example, to illuminate the tissue-engaging head of device 20 and/or the surgical field adjacent device 20. A transparent, semi-transparent or translucent tissue-engaging head may be illuminated merely by placement of the end of a light pipe or other light source adjacent the tissue-engaging head of device 20. The illumination source may be powered by AC current, DC current, or it may be battery powered either by a disposable or re-chargeable battery. The illumination source may provide UV, IR and/or visible light. The illumination source may be a laser. The illumination device may be incorporated into tissue-engaging device 20 or it may be incorporated into a separate device. A separate illumination device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. The illumination device may comprise one or more switches, e.g., a surgeon-controlled switch. One or more switches may be incorporated in or on the illumination device or any other location easily and quickly accessed by the surgeon for regulation of the illumination device by the surgeon. A switch may be, for example, a hand switch, a foot switch, or a voice-activated switch comprising voice-recognition technologies. A switch may be physically wired to the illumination device or it may be a remote control switch.

The tissue-engaging device 20, suction source 30, fluid source 40, energy source 50, sensor 60, processor 70, drug delivery device and/or illumination device may be slaved to a robotic system or a robotic system may be slaved to tissue-engaging device 20, suction source 30, fluid source 40, energy source 50, sensor 60, processor 70, drug delivery device and/or illumination device. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures. In general, robotic systems may include head-mounted displays that integrate 3-D visualization of surgical anatomy and related diagnostic and monitoring data, miniature high-resolution 2-D and 3-D digital cameras, a computer, a high power light source and a standard video monitor.

A medical procedure wherein system 10 may be used may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. Alternatively, the medical procedure may be surgery performed on another organ of the body. The term "medical procedure" may mean any one or more medical or surgical procedures such as, for example cardiac surgery, performed with or without cardiopulmonary bypass (CPB) circuits, heart valve repair, heart valve replacement, MAZE procedures, transmyocardial revascularization (TMR), CABG procedures, anastomosis procedures, non-surgical procedures, endoscopic procedures, non-invasive procedures, invasive procedures, port-access procedures, fluoroscopic procedures, beating heart surgery, vascular surgery, neurosurgery, electrophysiology procedures, diagnostic and therapeutic procedures, ablation procedures, ablation of arrhythmias, endovascular procedures, treatment of one or more organs and/or vessels, treatment of the heart, aneurysm repair, aortic aneurysm repairs, imaging procedures of the heart and great vessels, CAT scan procedures, MRI procedures, cardiograms, pharmacological therapies, drug delivery procedures, delivery of biological agents, gene therapies, cellular therapies, cancer therapies, radiation therapies, genetic, cellular, tissue and/or organ manipulation or transplantation procedures, coronary angioplasty procedures, placement or delivery of coated or noncoated stents, LVAD procedures, lead placement procedures, placement of cardiac reinforcement devices, placement of cardiac assistance devices, atherectomy procedures, atherosclerotic plaque manipulation and/or removal procedures, emergency procedures, cosmetic procedures, reconstructive surgical procedures, biopsy procedures, autopsy procedures, surgical training procedures, birthing procedures, congenital repair procedures, and medical procedures that require positioning one or more organs and/or tissues. The patient may be positioned for a medical procedure on their back, on their back with right or left side elevated or sitting up. The patient's right and/or left arm may be positioned out of the way to the side, elevated or lowered. The pericardial sac may be opened in any of a number of standard ways. The pericardial sac can be opened with a surgical tool in a long vertical incision extending from near the IVC to the posterior sternal table near the diaphragm. The incision may also extend horizontally to allow for more heart rotation. The free edges are then grasped with instruments inserted through the chest wall or subxiphoid space. The instruments themselves or sutures passed through the free edges are then pulled to open the incision and expose the heart within the chest. The instruments or sutures can be secured to the patient's chest wall or secured on an external mounting rail to hold the pericardial sac taut. Holding the sac taut allows easier access to the heart's surface. Also, by manipulating the instruments or sutures the heart can be rolled to one side or the other side in order to present various surfaces of the heart. Space can be created within the chest to allow more room to insert and operate instruments and to reposition the heart. The space can be created through gas insufflation to pressurize the chest interior, by use of an expanding structure within the chest wall and/or by hooking a portion of the rib cage and applying traction to expand the rib cage.

An endotracheal tube comprising one or more electrodes may be positioned in a patient's trachea. The endotracheal tube may be connected to a breathing regulator. The electrodes of the endotracheal tube may be used to stimulate the patient's vagal nerve thereby slowing or stopping the patient's heart. The patient may be given drugs as described above to help stop the beating of the heart and/or to prevent "escape" beats. Following vagal stimulation, the heart may be paced via device 20. The electrodes of the endotracheal tube may be coupled to processor 70 and energy source 50 via leads.

A nerve stimulator may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced, thereby maintaining a normal cardiac output. Vagal stimulation, alone or in combination with electrical pacing, may be used selectively and intermittently to allow a surgeon to perform a medical procedure, such as a CABG procedure, and yet still allow the heart itself to supply blood circulation to the body while one or more tissue-engaging devices 20 are used to position and/or stabilize an area of the heart. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Jonkman, which is incorporated herein by reference in its entirety.

The system 10 may be used for creating space in a surgical field. For example, tissue-engaging device 20 may be used to grasp and position the pericardium away from the surface of the heart thereby creating space between the surface of the heart and the pericardium. This type of procedure may be termed "tenting". Tissue-engaging device 20 may be used to grasp and position a heart away from a rib cage, for example in an endoscopic procedure, thereby creating space for a surgeon to work between the heart and the rib cage. Tissue-engaging device 20 may be used to grasp and position a heart away from other adjacent or nearby organs thereby creating space for a surgeon to work.

The medical procedure may include the use of one or more tissue stabilization devices, e.g., the "OCTOPUS 3"™ which is marketed by Medtronic, Inc., Minneapolis, Minn. USA. See, also, tissue stabilizers disclosed in U.S. Pat. Nos. 5,836,311; 5,927,284 and 6,015,378, co-assigned U.S. patent application Ser. No. 09/396,047, filed Sep. 15, 1999; and Ser. No. 09/678,203, filed Oct. 2, 2000, and European Patent Publication No. EP 0 993 806. These patents are assigned to Medtronic, Inc. and are incorporated herein by reference. Tissue-engaging device 20 of system 10 may be used in a medical procedure, e.g., a CABG procedure, in combination with a tissue stabilizer.

The medical procedure may include the use of one or more tissue ablation devices. Tissue-engaging device 20 of system 10 may be used in a medical procedure, e.g., an ablation procedure, in combination with a tissue ablation device. Device 20 may be attached to rail fixed to a patient's bed. Tissue ablation devices may be used to ablate tissue located within a body cavity, such as the endocardial or epicardial tissue of the heart. Other body organ tissue, such as the liver, lungs or kidney, may also be positioned and/or ablated. Other tissue types may be ablated including skin, muscle or even cancerous tissue or abnormal tissue growth.

The tissue-engaging device 20 can also be used to manipulate a beating heart in cardiac surgery procedures that utilize a greater than 4 cm thoracotomy for access to the heart.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A heart positioning device for moving a heart to a non-physiological orientation comprising:
    a suction head comprising a flexible, resilient material that may be compressed and resiliently return to its original shape and may flex to permit the suction head to engage and conform to a target tissue on the surface of the heart, the suction head having a vacuum passageway in fluid communication with the suction head to apply suction between the suction head and the target tissue on the surface of the heart;
a shaft having a vacuum lumen extending therethrough, the shaft coupled at a distal end to the suction head by a movable joint;
a handle coupled to a proximal end of the shaft for remote manipulation of the position of the suction head to effect movement of the heart to a non-physiological orientation; and
means on a proximal portion of the heart positioning device for remotely bending the movable joint from a first position in which the suction head is axially aligned with the shaft to a second, position in which the suction head is axially unaligned with the shaft.

2. A heart positioning device according to claim 1 wherein the suction head includes at least three resilient lobes in fluid communication with the vacuum passageway.

3. A heart positioning device according to claim 1 wherein the suction head is resiliently compressible from a first, uncompressed condition, to a second, compressed condition upon application of a constraint.

4. A heart positioning device according to claim 3 wherein the suction head is adapted at its second, compressed condition for slideable introduction of the compressed suction head through a port.

5. A heart positioning device according to claim 3 wherein the suction head in its compressed condition is adapted to resiliently return to the first, uncompressed condition upon release of the constraint.

6. A heart positioning device according to claim 1 wherein the means for remotely bending the movable joint comprises a wire.

7. A heart positioning device according to claim 6 wherein the means for bending the movable joint comprises spring means.

8. A heart positioning device according to claim 1 further comprising means for locking the position of the movable joint in the second, position.

9. A heart positioning device according to claim 1 wherein the second position is about 90 degrees from the first position.

10. A heart positioning device for moving a heart to a non-physiological orientation comprising:
a suction head having at least three lobes comprising a flexible, resilient material that may be compressed and resiliently return to its original shape and may flex to permit the suction head to engage and conform to a target tissue on the surface of the heart, the suction head having a vacuum passageway in fluid communication with the head to apply suction between the suction head and the surface of the heart;
a shaft having a vacuum lumen extending therethrough, the shaft coupled at a distal end to the suction head;
a handle coupled to a proximal end of the shaft for remote manipulation of the position of the suction head to effect movement of the heart to a non-physiological orientation; and
a sleeve slideably positioned on the shaft and sized to receive the suction head in a compressed condition such that the sleeve may be slideably advanced over the shaft to capture the suction head at the distal end thereof by allowing the lobes to be drawn against one another and also slideably released from capture with the sleeve by advancing the suction head distally from the sleeve such that the suction head resiliently returns to an uncompressed condition.

11. A heart positioning device according to claim 10 wherein the suction head is adapted at its compressed condition for slideable introduction of the compressed suction head through a port.

12. A heart positioning device according to claim 10 wherein the positioning device includes a retaining member for retaining the sleeve in a proximal position on the shaft.

13. A heart positioning device according to claim 10 wherein the sleeve is adapted for use as a port extending within an incision into a chest cavity of a patient.

14. A heart positioning device according to claim 10 wherein the sleeve is adapted to capture the suction head when the suction head is axially aligned with the shaft.

15. A heart positioning device for moving a heart to a non-physiological orientation comprising:
a suction head having at least three lobes comprising a flexible, resilient material that may be compressed and resiliently return to its original shape and may flex to permit the suction head to engage and conform to a target tissue on the surface of the heart, the suction head having a vacuum passageway in fluid communication with the suction head to apply suction between the suction head and the surface of the heart;
a shaft having a vacuum lumen extending therethrough, the shaft coupled at a distal end to the suction head;
a handle coupled to a proximal end of the shaft for remote manipulation of the position of the suction head to effect movement of the heart to a non-physiological orientation;
a sleeve slideably positioned on the shaft such that the suction head may be advanced or retracted with respect to the sleeve by manipulation of the handle; and
a retaining member for retaining the sleeve in a proximal position on the shaft.

16. A heart positioning device according to claim 15 wherein the sleeve is adapted for use as a port extending within an incision into a chest cavity of a patient.

17. A method of performing a surgical procedure on a heart, comprising:
providing a heart positioning device having a suction head comprising a flexible, resilient material that may be compressed and resiliently return to its original shape and may flex to permit the suction head to engage and conform to a target tissue on the surface of the heart, the suction head having a vacuum passageway in fluid communication with the suction head to apply suction between the suction head and the surface of the heart, a shaft having a vacuum lumen extending therethrough coupled at a distal end to the suction head by a movable joint and a handle coupled to a proximal end of the shaft;
introducing the suction head of the positioning device into a chest cavity of a patient through an incision by resiliently compressing the suction head from a first, uncompressed condition, to a second, compressed condition;
remotely changing the position of the suction head from a first position axially aligned with the shaft to a second, unaligned position by manipulating the movable joint from outside the chest cavity of the patient while the suction head is within the chest cavity;
engaging the heart with the suction head;
positioning the heart into a non-physiological orientation; and
performing a surgical procedure on the heart.

18. A method according to claim 17 wherein introducing the suction head includes compressing at least three resilient lobes of the suction head such that the lobes are drawn against one another.

19. A method according to claim 17 wherein the suction head is introduced into the chest cavity of the patient by slideably introducing it through a port.

20. A method according to claim 17 wherein the movable joint is remotely manipulated by activating a wire.

21. A method according to claim 17 wherein the movable joint is remotely manipulated from a control on the handle.

22. A method according to claim 17 further comprising returning the head from the second, unaligned position toward the first, axially aligned position and removing the suction head from the chest cavity through the incision.

23. A method according to claim 17 further comprising securing the position of the heart positioning device prior to the surgical procedure and releasing the position of the heart positioning device after the procedure.

24. A method according to claim 23 wherein securing the position of the heart positioning device is accomplished by clamping the heart positioning device to an arm.

25. A method according to claim 23 wherein securing the position of the heart positioning device is accomplished by actuating an arm attached to the heart positioning device to render the arm rigid.

26. A method of performing a surgical procedure on a heart, comprising:
providing a heart positioning device having a suction head comprising a flexible, resilient material that may be compressed and resiliently return to its original shape and may flex to permit the suction head to engage and conform to a target tissue on the surface of the heart, the suction head having a vacuum passageway in fluid communication with the suction head to apply suction between the suction head and the surface of the heart, a shaft having a vacuum lumen extending therethrough coupled at a distal end to the suction head, a handle coupled to a proximal end of the shaft and a sleeve slideably positioned on the shaft;
advancing the sleeve along the shaft to receive the suction head in a compressed condition;
introducing the sleeve and compressed suction head of the positioning device into an incision extending into a chest cavity of a patient;
advancing the suction head from the sleeve such that it achieves an uncompressed condition;
engaging the heart with the suction head;
positioning the heart into a non-physiological orientation; and performing a surgical procedure on the heart.

27. A method according to claim 26 wherein engaging the heart with the suction head includes engaging the heart with at least three resilient lobes of the suction head.

28. A method according to claim 26 wherein positioning of the heart is accomplished by remotely manipulating the suction head by moving the handle.

29. A method according to claim 26 further comprising securing the position of the heart positioning device prior to the surgical procedure and releasing the position of the heart positioning device after the procedure.

30. A method according to claim 29 wherein securing the position of the heart positioning device is accomplished by clamping the heart positioning device to an arm.

31. A method according to claim 29 wherein securing the position of the heart positioning device is accomplished by actuating an arm attached to the heart positioning device to render the arm rigid.

32. A method of performing a surgical procedure on a heart, comprising:
providing a heart positioning device having a suction head comprising a flexible, resilient material that may be compressed and resiliently return to its original shape and may flex to permit the suction head to engage and conform to a target tissue on the surface of the heart, the suction head having a vacuum passageway in fluid communication with the suction head to apply suction between the suction head and the surface of the heart, a shaft having a vacuum lumen extending therethrough coupled at a distal end to the suction head, a handle coupled to a proximal end of the shaft and a sleeve slideably positioned on the shaft;
advancing the sleeve long the shaft to receive the suction head in a compressed condition;
introducing the sleeve and compressed suction head of the positioning device at least partially into a port extending into a chest cavity of a patient;
advancing the suction head from the sleeve into the port and into the chest cavity such that it achieves an uncompressed condition;
engaging the heart with the positioning device;
positioning the heart into a non-physiological orientation; and
performing a surgical procedure on the heart.

33. A method according to claim 32 wherein engaging the heart with the suction head includes engaging the heart with at least three resilient lobes of the suction head.

34. A method according to claim 32 wherein positioning of the heart is accomplished by remotely manipulating the suction head by moving the handle.

35. A method according to claim 32 further comprising securing the position of the heart positioning device prior to the surgical procedure and releasing the position of the heart positioning device after the procedure.

36. A method according to claim 35 wherein securing the position of the heart positioning device is accomplished by clamping the heart positioning device to an arm.

37. A method according to claim 35 wherein securing the position of the heart positioning device is accomplished by actuating an arm attached to the heart positioning device to render the arm rigid.

38. A system for performing a medical procedure comprising:
a suction head comprising a flexible, resilient material that may be compressed and resiliently return to its original shape and may flex to permit the suction head to engage and conform to a target tissue on the surface of a heart, the suction head having a vacuum passageway in fluid communication with the suction head to apply suction between the suction head and the surface of the heart; a shaft having a vacuum lumen extending therethrough, the shaft coupled at a distal end by a movable joint to the suction head such that the suction head can be moved from a first position axially aligned with the shaft to a second, unaligned position by manipulating a control which is remote from the suction head to effect bending of the movable joint; a handle coupled to a proximal end of the shaft for remote manipulation of the position of the suction head to effect movement of the heart to a non-physiological orientation;
a port adapted to receive the suction head with the suction head in a compressed condition when the suction head is in the first, axially aligned condition; and a suction source in fluid communication with the heart positioning device.

39. A system for performing a medical procedure comprising:

a suction head having at least three lobes comprising a flexible resilient material that may be compressed and resiliently return to its original shape and may flex to permit the suction head to engage and conform to a target tissue on the surface of a heart, the suction head having a vacuum passageway in fluid communication with the suction head to apply suction between the suction head and the surface of the heart; a shaft having a vacuum lumen extending therethrough, the shaft coupled at a distal end to the suction head, a handle coupled to a proximal end of the shaft for remote manipulation of the position of the suction head to effect movement of the heart to a non-physiological orientation and a sleeve slideably positioned on the shaft and sized to receive the suction head in a compressed condition such that the sleeve may be slideably advanced over the shaft to capture the suction head at the distal end thereof;

a port adapted to receive at least a portion of the sleeve and the suction head with the suction head in a compressed condition within the sleeve with the lobes drawn against one another; and a suction source in fluid communication with the heart positioning device.

\* \* \* \* \*